(12) United States Patent
Kladakis et al.

(10) Patent No.: US 8,137,686 B2
(45) Date of Patent: Mar. 20, 2012

(54) NONWOVEN TISSUE SCAFFOLD

(75) Inventors: Stephanie M. Kladakis, Watertown, MA (US); Joseph J. Hammer, Bridgewater, NJ (US); Dhanuraj Shetty, Somerset, NJ (US); Sridevi Dhanaraj, Raritan, NJ (US)

(73) Assignee: DePuy Mitek, Inc., Raynham, MA (US)

( * ) Notice: Subject to any disclaimer, the term of this patent is extended or adjusted under 35 U.S.C. 154(b) by 639 days.

(21) Appl. No.: 10/828,838

(22) Filed: Apr. 20, 2004

(65) Prior Publication Data

US 2005/0232967 A1   Oct. 20, 2005

(51) Int. Cl.
   *A61F 2/00*   (2006.01)
(52) U.S. Cl. .......................... 424/423; 424/426
(58) Field of Classification Search .................. None
   See application file for complete search history.

(56) References Cited

U.S. PATENT DOCUMENTS

| | | |
|---|---|---|
| 206,200 A | 7/1878 | Stewart |
| 224,226 A | 2/1880 | Rind |
| 259,260 A | 6/1882 | Baeyer et al. |
| 3,272,204 A | 9/1966 | Artandi |
| 3,739,402 A | 6/1973 | Cooley et al. |
| 3,812,017 A | 5/1974 | Santangelo et al. |
| 3,857,932 A | 12/1974 | Shepherd et al. |
| 4,045,418 A | 8/1977 | Sinclair |
| 4,057,537 A | 11/1977 | Sinclair |
| 4,105,034 A | 8/1978 | Shalaby et al. |
| 4,130,639 A | 12/1978 | Shalaby et al. |
| 4,130,689 A | 12/1978 | Costa, Jr. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,344,193 A | 8/1982 | Kenny |
| 4,520,821 A | 6/1985 | Schmidt et al. |
| 4,553,272 A | 11/1985 | Mears |
| 4,585,458 A | 4/1986 | Kurland |
| 4,597,766 A | 7/1986 | Hilal |
| 4,609,551 A | 9/1986 | Caplan et al. |
| 4,728,329 A | 3/1988 | Mansat et al. |
| 4,801,299 A | 1/1989 | Brendel et al. |
| 4,837,285 A | 6/1989 | Berg et al. |
| 4,902,508 A | 2/1990 | Badylak et al. |
| 4,946,377 A | 8/1990 | Kovach |
| 5,007,934 A | 4/1991 | Stone |
| 5,041,138 A | 8/1991 | Vacanti et al. |
| 5,053,050 A | 10/1991 | Itay |
| 5,061,281 A | 10/1991 | Mares et al. |
| 5,078,744 A | 1/1992 | Chvapil |

(Continued)

FOREIGN PATENT DOCUMENTS

AU    717552    3/1998

(Continued)

OTHER PUBLICATIONS

Boland et al., J Macromol Sci-Pure Appl Chem. 2001;A38(12):1231-1243.*

(Continued)

*Primary Examiner* — Cherie M Woodward

(57) ABSTRACT

A biocompatible meniscal repair device is disclosed. The tissue repair device includes a scaffold adapted to be placed in contact with a defect in a meniscus, the scaffold comprising a high-density, dry laid nonwoven polymeric material and a biocompatible foam. The scaffold provides increased suture pull-out strength.

26 Claims, 27 Drawing Sheets

U.S. PATENT DOCUMENTS

| | | | |
|---|---|---|---|
| 5,108,989 A | 4/1992 | Amento et al. | |
| 5,147,400 A | 9/1992 | Kaplan et al. | |
| 5,176,708 A | 1/1993 | Frey et al. | |
| 5,206,023 A | 4/1993 | Hunziker | |
| 5,258,028 A | 11/1993 | Ersek et al. | |
| 5,263,984 A | 11/1993 | Li et al. | |
| 5,306,311 A | 4/1994 | Stone et al. | |
| 5,326,357 A | 7/1994 | Kandel | |
| 5,366,756 A | 11/1994 | Chesterfield et al. | |
| 5,425,766 A | 6/1995 | Bowald | |
| 5,443,950 A | 8/1995 | Naughton et al. | |
| 5,445,833 A | 8/1995 | Badylak et al. | |
| 5,455,041 A | 10/1995 | Genco et al. | |
| 5,464,929 A | 11/1995 | Bezwada et al. | |
| 5,468,253 A | 11/1995 | Bezwada et al. | |
| 5,480,827 A | 1/1996 | Guillemin et al. | |
| 5,487,897 A | 1/1996 | Polson et al. | |
| 5,514,181 A | 5/1996 | Light et al. | |
| 5,514,378 A | 5/1996 | Mikos et al. | |
| 5,571,189 A | 11/1996 | Kuslich | |
| 5,577,517 A | 11/1996 | Bonutti | |
| 5,589,176 A | 12/1996 | Seare, Jr. | |
| 5,595,751 A | 1/1997 | Bezwada et al. | |
| 5,597,579 A | 1/1997 | Bezwada et al. | |
| 5,607,687 A | 3/1997 | Bezwada et al. | |
| 5,612,028 A | 3/1997 | Sackier et al. | |
| 5,618,552 A | 4/1997 | Bezwada et al. | |
| 5,620,698 A | 4/1997 | Bezwada et al. | |
| 5,624,463 A | 4/1997 | Stone et al. | |
| 5,632,745 A | 5/1997 | Schwartz | |
| 5,645,850 A | 7/1997 | Bezwada et al. | |
| 5,648,088 A | 7/1997 | Bezwada et al. | |
| 5,654,135 A | 8/1997 | Tinois et al. | |
| 5,656,492 A | 8/1997 | Glowacki et al. | |
| 5,677,355 A | 10/1997 | Shalaby et al. | |
| 5,681,353 A | 10/1997 | Li et al. | |
| 5,697,976 A | 12/1997 | Chesterfield et al. | |
| 5,698,213 A | 12/1997 | Jamiolkowski et al. | |
| 5,700,583 A | 12/1997 | Jamiolkowski et al. | |
| 5,709,854 A | 1/1998 | Griffith-Cima et al. | |
| 5,711,960 A | 1/1998 | Shikinami | |
| 5,720,969 A | 2/1998 | Gentile et al. | |
| 5,723,331 A | 3/1998 | Tubo et al. | |
| 5,735,903 A | 4/1998 | Li et al. | |
| 5,736,372 A | 4/1998 | Vacanti et al. | |
| 5,755,791 A | 5/1998 | Whitson et al. | |
| 5,759,190 A | 6/1998 | Vibe-Hansen et al. | |
| 5,766,631 A | 6/1998 | Arnold | |
| 5,769,899 A | 6/1998 | Schwartz et al. | |
| 5,786,217 A | 7/1998 | Tubo et al. | |
| 5,830,493 A | 11/1998 | Yokota et al. | |
| 5,837,235 A | 11/1998 | Mueller et al. | |
| 5,842,477 A | 12/1998 | Naughton et al. | |
| 5,855,608 A | 1/1999 | Brekke et al. | |
| 5,859,150 A | 1/1999 | Jamiolkowski et al. | |
| 5,891,558 A | 4/1999 | Bell et al. | |
| 5,902,741 A | 5/1999 | Purchio et al. | |
| 5,904,716 A | 5/1999 | Gendler | |
| 5,904,717 A | 5/1999 | Brekke et al. | |
| 5,914,121 A | 6/1999 | Robey et al. | |
| 5,922,025 A | 7/1999 | Hubbard | |
| 5,964,805 A | 10/1999 | Stone | |
| 5,968,096 A | 10/1999 | Whitson et al. | |
| 5,980,889 A | 11/1999 | Butler et al. | |
| 5,989,269 A | 11/1999 | Vibe-Hansen et al. | |
| 5,990,194 A | 11/1999 | Dunn et al. | |
| 5,990,378 A | 11/1999 | Ellis | |
| 6,001,352 A | 12/1999 | Boyan et al. | |
| 6,001,394 A | 12/1999 | Daculsi et al. | |
| 6,005,161 A * | 12/1999 | Brekke et al. | 424/422 |
| 6,027,742 A | 2/2000 | Lee et al. | |
| 6,042,610 A | 3/2000 | Li et al. | |
| 6,054,122 A | 4/2000 | MacPhee et al. | |
| 6,077,989 A | 6/2000 | Kandel et al. | |
| 6,080,579 A | 6/2000 | Hanley, Jr. et al. | |
| 6,096,532 A | 8/2000 | Armstrong et al. | |
| 6,103,255 A | 8/2000 | Levene et al. | |
| 6,110,209 A | 8/2000 | Stone | |
| 6,110,212 A | 8/2000 | Gregory | |
| 6,117,166 A | 9/2000 | Winston et al. | |
| 6,120,514 A | 9/2000 | Vibe-Hansen et al. | |
| 6,121,042 A | 9/2000 | Peterson et al. | |
| 6,123,727 A | 9/2000 | Vacanti et al. | |
| 6,132,463 A | 10/2000 | Lee et al. | |
| 6,132,468 A | 10/2000 | Mansmann | |
| 6,139,578 A | 10/2000 | Lee et al. | |
| 6,140,039 A | 10/2000 | Naughton et al. | |
| 6,143,293 A | 11/2000 | Weiss et al. | |
| 6,153,292 A | 11/2000 | Bell et al. | |
| 6,156,068 A | 12/2000 | Walter et al. | |
| 6,165,217 A * | 12/2000 | Hayes | 623/11.11 |
| 6,176,880 B1 | 1/2001 | Plouhar et al. | |
| 6,179,840 B1 | 1/2001 | Bowman | |
| 6,179,872 B1 | 1/2001 | Bell et al. | |
| 6,180,007 B1 | 1/2001 | Gentile et al. | |
| 6,183,737 B1 | 2/2001 | Zaleske et al. | |
| 6,187,053 B1 | 2/2001 | Minuth | |
| 6,187,329 B1 | 2/2001 | Agrawal et al. | |
| 6,197,061 B1 | 3/2001 | Masuda et al. | |
| 6,197,325 B1 | 3/2001 | MacPhee et al. | |
| 6,200,606 B1 | 3/2001 | Peterson et al. | |
| 6,214,045 B1 | 4/2001 | Corbitt, Jr. et al. | |
| 6,214,055 B1 | 4/2001 | Simionescu et al. | |
| 6,242,247 B1 | 6/2001 | Rieser et al. | |
| 6,251,673 B1 | 6/2001 | Winkler | |
| 6,277,151 B1 | 8/2001 | Lee et al. | |
| 6,283,980 B1 | 9/2001 | Vibe-Hansen et al. | |
| 6,287,340 B1 | 9/2001 | Altman et al. | |
| 6,291,240 B1 | 9/2001 | Mansbridge et al. | |
| 6,306,177 B1 | 10/2001 | Felt et al. | |
| 6,306,424 B1 | 10/2001 | Vyakarnam et al. | |
| 6,316,692 B1 | 11/2001 | Readhead et al. | |
| 6,319,712 B1 | 11/2001 | Meenen et al. | |
| 6,331,312 B1 | 12/2001 | Lee et al. | |
| 6,333,029 B1 | 12/2001 | Vyakarnam et al. | |
| 6,365,149 B2 | 4/2002 | Vyakarnam et al. | |
| 6,378,527 B1 | 4/2002 | Hungerford et al. | |
| 6,378,572 B1 | 4/2002 | Neubauer et al. | |
| 6,379,367 B1 | 4/2002 | Vibe-Hansen et al. | |
| 6,464,729 B1 | 10/2002 | Kandel | |
| 6,485,723 B1 | 11/2002 | Badylak et al. | |
| 6,489,165 B2 | 12/2002 | Bhatnagar et al. | |
| 6,511,958 B1 | 1/2003 | Atkinson et al. | |
| 6,530,956 B1 | 3/2003 | Mansmann | |
| 6,534,084 B1 | 3/2003 | Vyakarnam et al. | |
| 6,541,024 B1 | 4/2003 | Kadiyala et al. | |
| 6,551,355 B1 | 4/2003 | Lewandrowski et al. | |
| 6,569,172 B2 | 5/2003 | Asculai et al. | |
| 6,592,588 B1 | 7/2003 | Bobic et al. | |
| 6,599,323 B2 * | 7/2003 | Melican et al. | 623/23.72 |
| 6,605,294 B2 | 8/2003 | Sawhney | |
| 6,626,950 B2 | 9/2003 | Brown et al. | |
| 6,727,224 B1 | 4/2004 | Zhang et al. | |
| 6,773,458 B1 | 8/2004 | Brauker et al. | |
| 6,783,712 B2 | 8/2004 | Slivka et al. | |
| 6,840,962 B1 | 1/2005 | Vacanti et al. | |
| 6,852,330 B2 * | 2/2005 | Bowman et al. | 424/426 |
| 6,866,681 B2 | 3/2005 | Laboureau et al. | |
| 6,884,428 B2 * | 4/2005 | Binette et al. | 424/422 |
| 6,886,568 B2 | 5/2005 | Frondoza et al. | |
| 6,886,569 B2 | 5/2005 | Chervitz et al. | |
| 7,208,177 B2 | 4/2007 | Geistlich et al. | |
| 7,262,020 B2 | 8/2007 | Hellerstein | |
| 7,316,822 B2 | 1/2008 | Binette et al. | |
| 7,824,701 B2 | 11/2010 | Binette et al. | |
| 7,875,296 B2 | 1/2011 | Binette et al. | |
| 7,901,461 B2 | 3/2011 | Harmon et al. | |
| 2001/0014475 A1 | 8/2001 | Frondoza et al. | |
| 2001/0016353 A1 | 8/2001 | Janas et al. | |
| 2001/0016772 A1 | 8/2001 | Lee et al. | |
| 2001/0023373 A1 | 9/2001 | Plouhar et al. | |
| 2001/0038848 A1 | 11/2001 | Donda et al. | |
| 2001/0039453 A1 | 11/2001 | Gresser et al. | |
| 2001/0051834 A1 | 12/2001 | Frondoza et al. | |
| 2001/0053353 A1 | 12/2001 | Griffith et al. | |
| 2001/0053839 A1 | 12/2001 | Noishiki et al. | |
| 2002/0006428 A1 | 1/2002 | Mahmood et al. | |

| | | | | | | |
|---|---|---|---|---|---|---|
| 2002/0009477 A1 | 1/2002 | Mahmood et al. | EP | 1027897 A1 | 8/2000 | |
| 2002/0009805 A1 | 1/2002 | Nevo et al. | EP | 1 064 958 | 1/2001 | |
| 2002/0009806 A1 | 1/2002 | Hicks, Jr. | EP | 1 167 517 | 1/2002 | |
| 2002/0013627 A1 | 1/2002 | Geistlich et al. | EP | 1177800 A1 | 2/2002 | |
| 2002/0015719 A1 | 2/2002 | Kellner et al. | EP | 1 216 718 A | 6/2002 | |
| 2002/0022883 A1 | 2/2002 | Burg | EP | 1348451 A1 | 10/2003 | |
| 2002/0022884 A1 | 2/2002 | Mansmann | EP | 1 405 649 | 4/2004 | |
| 2002/0028192 A1 | 3/2002 | Dimitrijevich et al. | EP | 1410811 A1 | 4/2004 | |
| 2002/0029055 A1 | 3/2002 | Bonutti | EP | 1506790 A1 | 2/2005 | |
| 2002/0062151 A1 | 5/2002 | Altman | EP | 1537839 A1 | 6/2005 | |
| 2002/0082631 A1 | 6/2002 | Bonutti | EP | 1 604 622 | 12/2005 | |
| 2002/0083479 A1 | 6/2002 | Winston et al. | FR | 2688690 A1 | 9/1993 | |
| 2002/0091403 A1 | 7/2002 | Bonutti | GB | 1008193 A | 10/1965 | |
| 2002/0091406 A1 | 7/2002 | Bonutti | JP | 63-203154 A | 8/1988 | |
| 2002/0099401 A1 | 7/2002 | Bonutti | JP | 02-052648 | 2/1990 | |
| 2002/0099448 A1 | 7/2002 | Hiles et al. | JP | 2143945 | 12/1990 | |
| 2002/0107570 A1 | 8/2002 | Sybert et al. | JP | 19900227442 A | 4/1992 | |
| 2002/0119177 A1 | 8/2002 | Bowman et al. | JP | 19900256824 A | 5/1992 | |
| 2002/0127265 A1* | 9/2002 | Bowman et al. ............ 424/426 | JP | 19910261753 A | 7/1993 | |
| 2002/0133229 A1 | 9/2002 | Laurencin et al. | JP | 19920094329 A | 11/1993 | |
| 2002/0133235 A1 | 9/2002 | Hungerford et al. | JP | 10234844 A | 9/1998 | |
| 2002/0150604 A1 | 10/2002 | Yi et al. | JP | 19980129048 A | 11/1999 | |
| 2002/0151975 A1 | 10/2002 | Farr et al. | JP | 19980319783 A | 5/2000 | |
| 2002/0173558 A1 | 11/2002 | Williams et al. | JP | 2001129073 A | 5/2001 | |
| 2002/0176893 A1 | 11/2002 | Wironen et al. | JP | 2003320008 A | 11/2003 | |
| 2002/0177224 A1 | 11/2002 | Madry et al. | JP | 2004008437 A | 1/2004 | |
| 2003/0003153 A1 | 1/2003 | Asculai et al. | JP | 20020165345 A | 1/2004 | |
| 2003/0004578 A1 | 1/2003 | Brown et al. | JP | 2004195103 | 7/2004 | |
| 2003/0012805 A1 | 1/2003 | Chen et al. | RU | 2187261 | 8/2002 | |
| 2003/0023316 A1 | 1/2003 | Brown et al. | SU | 1535542 | 1/1990 | |
| 2003/0026787 A1 | 2/2003 | Fearnot et al. | WO | WO 86/00533 | 1/1986 | |
| 2003/0027332 A1 | 2/2003 | Lafrance et al. | WO | 92/06179 A1 | 4/1992 | |
| 2003/0033021 A1 | 2/2003 | Plouhar et al. | WO | 93/02718 A1 | 2/1993 | |
| 2003/0033022 A1 | 2/2003 | Plouhar et al. | WO | 93/11805 A1 | 6/1993 | |
| 2003/0036797 A1 | 2/2003 | Malaviya et al. | WO | WO 95/33821 | 12/1995 | |
| 2003/0036801 A1 | 2/2003 | Schwartz et al. | WO | 96/08277 A1 | 3/1996 | |
| 2003/0050709 A1 | 3/2003 | Noth et al. | WO | WO 97/30662 | 8/1997 | |
| 2003/0064917 A1 | 4/2003 | Crawford et al. | WO | WO 97/46665 | 12/1997 | |
| 2003/0075822 A1 | 4/2003 | Slivka et al. | WO | WO 98/48860 | 11/1998 | |
| 2003/0077311 A1 | 4/2003 | Vyakarnam et al. | WO | 98/53768 A1 | 12/1998 | |
| 2003/0078617 A1 | 4/2003 | Schwartz et al. | WO | 9905992 A1 | 2/1999 | |
| 2004/0024457 A1 | 2/2004 | Boyce et al. | WO | WO 99/16381 | 4/1999 | |
| 2004/0059416 A1 | 3/2004 | Murray et al. | WO | 9939724 A1 | 8/1999 | |
| 2004/0078077 A1 | 4/2004 | Binette et al. | WO | WO 99/47097 | 9/1999 | |
| 2004/0078090 A1 | 4/2004 | Binette et al. | WO | 99/59647 A1 | 11/1999 | |
| 2004/0219182 A1 | 11/2004 | Gomes et al. | WO | 0015248 A2 | 3/2000 | |
| 2004/0236424 A1 | 11/2004 | Berez et al. | WO | 0016381 | 3/2000 | |
| 2004/0267362 A1 | 12/2004 | Hwang et al. | WO | 00/69355 A1 | 11/2000 | |
| 2005/0002915 A1 | 1/2005 | Atala et al. | WO | 00/72782 A1 | 12/2000 | |
| 2005/0038520 A1 | 2/2005 | Binette et al. | WO | 0074741 A2 | 12/2000 | |
| 2005/0113937 A1 | 5/2005 | Binette et al. | WO | 0115753 A1 | 3/2001 | |
| 2005/0125077 A1 | 6/2005 | Harmon et al. | WO | 01/34065 A1 | 5/2001 | |
| 2005/0147645 A1 | 7/2005 | Budny | WO | WO 0185226 A1 * | 11/2001 | |
| 2005/0177249 A1 | 8/2005 | Kladakis et al. | WO | 02/00272 A2 | 1/2002 | |
| 2005/0234549 A1 | 10/2005 | Kladakis et al. | WO | 0205750 A2 | 1/2002 | |
| 2006/0067967 A1 | 3/2006 | Bowman et al. | WO | WO 02/30324 | 4/2002 | |
| 2006/0084930 A1 | 4/2006 | Dhanaraj et al. | WO | 02062357 A1 | 8/2002 | |
| 2006/0204439 A1 | 9/2006 | Hellerstein | WO | 02074356 A1 | 9/2002 | |
| 2006/0223177 A1 | 10/2006 | Harris et al. | WO | 02/096268 A2 | 12/2002 | |
| 2006/0280768 A1 | 12/2006 | Hwang et al. | WO | 03/007784 A2 | 1/2003 | |
| 2006/0293760 A1 | 12/2006 | DeDeyne | WO | 03/007786 A2 | 1/2003 | |
| 2007/0031470 A1 | 2/2007 | Kladakis et al. | WO | 03/007787 A2 | 1/2003 | |
| 2007/0036767 A1 | 2/2007 | Mistry et al. | WO | 03/007788 A2 | 1/2003 | |
| 2007/0250177 A1 | 10/2007 | Bilbo | WO | 03/007790 A2 | 1/2003 | |
| 2008/0039955 A1 | 2/2008 | Hunziker | WO | 03/007805 A2 | 1/2003 | |
| 2011/0009963 A1 | 1/2011 | Binnette et al. | WO | 03/007839 A2 | 1/2003 | |
| 2011/0091517 A1 | 4/2011 | Binette et al. | WO | 03/007847 A1 | 1/2003 | |
| 2011/0097381 A1 | 4/2011 | Binette et al. | WO | 03007789 A2 | 1/2003 | |
| 2011/0177134 A1 | 7/2011 | Harmon et al. | WO | 03017826 A2 | 3/2003 | |
| | | | WO | 03/043674 A1 | 5/2003 | |
| | | | WO | 2004012782 A1 | 2/2004 | |

FOREIGN PATENT DOCUMENTS

| | | | |
|---|---|---|---|
| CA | 2247158 A1 | 8/1997 | |
| DE | 19812195 A1 | 9/1999 | |
| EP | 0145492 A2 | 6/1985 | |
| EP | 0 274 898 | 7/1988 | |
| EP | 0277678 A1 | 8/1988 | |
| EP | 0464163 A1 | 1/1992 | |
| EP | 0 562 864 | 9/1993 | |
| EP | 0 955 024 | 11/1999 | |

OTHER PUBLICATIONS

American Heritage Dictionary. Fourth Ed. 2000.—Isotropic.*
Tozum et al., J Canadian Dental Assoc. Nov. 2003 69(10):664-664h.*
Buschmann et al.. J. Orthop. Res. 1992;10:745-752.*
Albrecht et al., (Arch. Orthop. Trauma Surg. 1983:213-217).*

Thomas F. Deuel and Nan Zhang, "Growth Factors" in Principles of Tissue Engineering, Second Edition, Academic Press, 2000, pp. 129-141.

Sally R. Frenkel, Ph.D. and Paul E. Di Cesare, M.D., "Degradation and Repair of Articular Cartilage" in Frontiers in Bioscience, 4th ed., pp. 671-685, Oct. 15, 1999, pp. 1-32.

Keith J. Gooch et al., "Mechanical Forces and Growth Factors Utilized in Tissue Engineering" in Frontier in Tissue Engineering, Pergamon, 1998, Chapter II.3, pp. 61-82.

John A. Koski, M.D. et al., "Meniscal Injury and Repair", Orthopedic Clinics of North American, vol. 31, No. 3, Jul. 2000, pp. 419-435.

John A. Koski, M.D. et al., "Tissue-Engineered Ligament—Cells, Matrix, and Growth Factors" in Tissue Engineering in Orthopedic Surgery, vol. 31, No. 3, Jul. 2000, pp. 437-452.

Clemente Ibarra, M.D. et al. "Tissue-Engineered Meniscus—Cells and Matrix", in Tissue Engineering in Orthopedic Surgery, vol. 31, No. 3, Jul. 2000, pp. 411-418.

Stone, K. et al. "Meniscal Regeneration With Copolymeric Collagen Scaffolds" American Journal of Sports Medicine, 20(2):104-111 (1992).

Murray, M., et al. "The Migration of Cells from the Rup[tured Human Anterior Cruciate Ligament into Collagen-Glycosaminoglycan Regeneration Templated in Vitro" Biomaterials 22:2393-2402 (2001).

(Abstract Only) Caterson EJ., et al. "Three-Dimensional Cartilage Formation by Bone Marrow-Derived Cells Seeded in Polylactide/Alginate Amalgam" J Biomed Mater Res, 57(3):394-403 (2001).

(Abstract Only) Grigolo, B., et al. "Transplantation of Chondrocytes Seeded on a Hyaluronan Derivative (hyaff-11) into Cartilage Defects in Rabbits" Biomaterials 22(17):2417-2424 (2001).

(Abstract Only) van Susante JLC, et al. "Linkage of Chondroitin-sulfate to Type I Collagen Scaffolds Stimulates the Bioactivity of Seeded Chondrocytes in Vitro", Biomaterials, 22(17):2359-2369 (2001).

(Abstract Only) Hutmacher DW., "Scaffold Design and Fabrication Technologies for Engineering Tissues-State of the Art and future Prospectives", J Biomater Sci Polym Ed, 12(1):107-124 (2001).

(Abstract Only) Hutmacher DW., "Scaffolds in Tissue Engineering Bone and Cartilage", Biomaterials, 21(24):2529-2543 (2000).

(Abstract Only) Schreiber RE., et al. "A Method for Tissue Engineering of cartilage by Cell Seeding on Bioresorbable Scaffolds" Ann NY Acad Sci, 875:394-404 (1999).

(Abstract Only) Radice, M. "Hyaluronan-Based Biopolymers as delivery vehicles for BoneMarrow-Derived Mesenchymal Progenitors", J Biomed Mater Res, 50(2):101-9 (2000).

Albrecht, F., et al. Closure of Osteochondral Lesions Using Chondral Fragments and Fibrin Adhesive, Arch Orthop. Trauma Surg. (1983) 101:213-217.

Sampath, T.K., et al. In vitro transformation of mesenchymal cells derived from embryonic muscle into cartilage in response to extracellular matrix components of bone, Proc. Natl. Acad. Sci. USA vol. 81, pp. 3419-3423, Jun. 1984.

Eckersberger, M.D., Franz, "Circumferential tracheal replacement with costal cartilage", The Journal of Thoracic and Cardiovascular Surgery, 1987;94: pp. 175-180.

Matsuo, M.D., Kiyoshi et al., "Semiquantitative Correction of Post-traumatic Enophthalmos with Sliced Cartilage Grafts" Plastic and Reconstructive Surgery, vol. 83, No. 3, Postraumatic Enophthalmos, pp. 429-437.

Megumi, M.D., Yoshikazu, "Augmentation Rhinoplasty with Soft Tissue and Cartilage" Aesthetic Plastic Surgery, 1988, pp. 89-933.

Papadopulos, M.D., Angel, "Compound Implant to Projedt the Nasal Tip" Aesthetic Plastic Surgery, 1987, pp. 181-185.

Partial European Search Report, for EP 04 25 7515, mailed May 9, 2005.

Powers, Dennis L. et al., "A cartilagenous graft as an adjunct to finger joint implant arthroplasty" Journal of Biomedical Materials Research, vol. 19, 1985 pp. 509-518.

Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.

Trenite, M.D., G.J. Nolst et al., "Reimplantation of autologous septal cartilage in the growing nasal septum", Rhinology, 25, 1987, pp. 225-236.

De Groot J H et al: "Use of porous polyurethanes for meniscal reconstruction and meniscal prostheses", Biomaterials, Elsevier Publishers BV., Arking, CB. vol. 17, No. 2, 1996, pp. 163-173.

De Groot J H et al: "Meniscal tissue regeneration in porous 50/50 copoly (1- lactide/epsilon-caprolactone) implants" Biomaterials, Elsevier Science Publishers BV., Barking, GB, vol. 18, No. 8, (Apr. 1997), pp. 613-622.

Tienen T G et al: "A porous polymer scaffold for meniscal lesion repair—A study in dogs" Biomaterials, Elsevier Science Publishers BV., Barking, CG, vol. 24, No.14, (Jun. 2006), pp. 2541-2548.

European Search Report issued in European Application No. 07252617.1, Nov. 2, 2007.

Albrecht, F.H., "The Closure of Joint Cartilage Defects by Means of Cartilage Fragments and Fibrin Adhesive," Fortschr. Med. 101(37):1650-52 (1983).

European Search Report, for EP 03 25 6522, mailed Feb. 24, 2004.

Rossi, et al., "Embryonic Purkinje Cells Grafted on the Surface of the Cerebellar Cortex Integrate in the Adult Unlesioned Cerebellum," EP J. Neuroscience 4:589-93 (1992).

Solov'ev et al., "Functional Activity of Hepatocytes in Liver Fragments In Vitro as a Function if Fragment Size and Duration of Culturing" Bull Exp Biol Med. Jun. 2000;129(6):595-7.

Boland et. al., J. Macromol. Sci.-Pure Appl. Chem., 2001, A38(12), p. 1231-1243).

Microcellular Foams via Phase Separation, J. Vac. Sci. Technolol., A.T. Young, vol. 4(3), May/Jun. 1986.

Spaans et al. "Solvent-free fabrication of micro-porous polyurethane amide and polyurethane-urea scaffolds for repair and replacement of the knee joint meniscus" Journal of Biomaterials, vol. 21, No. 23, 2000, pp. 2453-2460.

Nioshiki Y., "A new trend in hybrid artificial organs" J. Artificial Organs, 1999, vol. 2: pp. 93-96.

Kemnitzer and Kohn, in the Handbook of Biodegradable Polymers, edited by Domb, et. al., Hardwood Academic Press, pp. 251-272 (1997).

Journal of Biomaterials Research, vol. 22, pp. 993-1009, 1988 by Cohn and Younes.

Polymer Preprints (ACS Division of Polymer Chemistry), vol. 30(1), p. 498, 1989 by Cohn.

Allcock in The Encyclopedia of Polymer Science, vol. 13, pp. 31-41, Wiley Intersciences, John Wiley & Sons, 1988.

Vandorpe, et al in the Handbook of Biodegradable Polymers, edited by Domb, et al., Hardwood Academic Press, pp. 161-182 (1997).

Bonisch, M., et al. "Septumredonstrucktion mit PDS-Folie" HNO 47: 1999 pp. 546-550.

Ikada, Yoshito, Handbook of Fiber Science and Technology, Edited by Menachem Lewin, Jack Preston, vol. III, Part B, Chapter 8, pp. 253, 289-295, Published by M. Dekker, 1983.

Kurashina, K. et al. "Osteogenesis in muscle with composite graft of hydroxyapatite and autogenous calvarial periosteum: a preliminary report" Biomaterials (1995) vol. 16, No. 2, pp. 119-123.

www.btc-bti.com/applications/cryogenicstorage.htm, 6 pgs, printed Jan. 11, 2010.

www.bio-medicine.org/medicine-technology-1/New-Study-Shows-Cloning-From-Dried-Cells-Now-Possible-2988-1/, 2 pgs, printed Jan. 11, 2010.

Chen G., Ushida T. and Tateishi T. "A hybrid network of synthetic polymer mesh and collagen sponge," Chem. Commun., 2000, 1505-1506.

European Search Report for EP 08075114.2, mailed May 12, 2010.

Heller: 'Handbook of Biodegradable Polymers', 1997, Hardwood Academic Press pp. 99-118.

U.S. Appl. No. 10/775,034 of Kladakis et al. (see Office Actions dated Nov. 30, 2006, Apr. 30, 2007, May 7, 2007, May 2, 2008, Dec. 11, 2008, Jul. 29, 2009, and Jan. 14, 2010).

U.S. Appl. No. 10/729,046 of Harmon et al. (see Office Actions dated Jun. 17, 2005, Dec. 19, 2005, Mar. 7, 2006, May 15, 2006, Nov. 8, 2006, Feb. 23, 2007, May 24, 2007, Mar. 27, 2008, Aug. 18, 2008, Oct. 2, 2008, Mar. 25, 2009, Jul. 27, 2009, Nov. 3, 2009, and Notice of Allowance dated Jun. 15, 2010).

U.S. Appl. No. 10/723,982 of Binette et al., now U.S. Patent No. 7,316,822 (see Office Actions dated Jul. 27, 2006, Jan. 4, 2007, Apr. 18, 2007, May 16, 2007, and Notice of Allowance dated Aug. 17, 2007).

U.S. Appl. No. 10/374,754 of Binette et al. (see Office Actions dated Mar. 24, 2006, Sep. 1, 2006, Feb. 26, 2007, May 15, 2007, Sep. 1, 2007, Mar. 18, 2008, Sep. 16, 2008, Dec. 4, 2008, Sep. 9, 2009, Dec. 18, 2009, and Notice of Allowance dated Jun. 21, 2010).

U.S. Appl. No. 10/374,772 of Gosiewska et al. (see Office Actions dated Apr. 19, 2006, Sep. 14, 2006, May 16, 2007, Dec. 3, 2007, Feruary 29, 2008, Sep. 2, 2008, Feb. 27, 2009, Jun. 8, 2009, and Jan. 4, 2010).

U.S. Appl. No. 10/828,838 of Dhanaraj et al. (see Office Actions dated May 4, 2007, Dec. 31, 2007, Mar. 19, 2008, Jun. 24, 2008, Oct. 16, 2008, Mar. 12, 2009, Jul. 21, 2009, Oct. 30, 2009, Mar. 10, 2010, and Notice of Allowance dated May 25, 2010).

U.S. Appl. No. 11/427,477 of Dhanaraj et al. (see Office Actions dated Aug. 8, 2008, Jan. 15, 2009, Mar. 24, 2009, Sep. 28, 2009, Mar. 10, 2010, and Notice of Allowance dated Jun. 8, 2010).

U.S. Appl. No. 10/610,362 of Malaviya et al. (see Office Actions dated Aug. 9, 2005, Feb. 3, 2006, Apr. 14, 2006, Jul. 31, 2006, Feb. 5, 2007, Apr. 12, 2007, Aug. 8, 2007, Jan. 28, 2008, Jul. 11, 2008, Oct. 10, 2008, Apr. 28, 2009, Jul. 13, 2009, Oct. 15, 2009, Mar. 26, 2010 and Jul. 14, 2010).

U.S. Appl. No. 09/747,488 of Bowman et al., now U.S. Patent No. 6,852,330 (see Office Actions dated Oct. 22, 2002, Mar. 12, 2003, Jul. 28, 2003, Feb. 12, 2004 and Notice of Allowance dated Sep. 28, 2004).

U.S. Appl. No. 10/022,182 of Melican et al., now abandoned (see Office Actions dated Nov. 17, 2003, May 5, 2004, Nov. 26, 2004, and Jun. 16, 2005).

U.S. Appl. No. 10/320,751 of Binette et al., now U.S. Patent No. 6,884,428(see Office Action dated May 3, 2004 and Notice of Allowance dated Oct. 20, 2004).

U.S. Appl. No. 11/280,189 of Bowman et al. (see Office Action dated Sep. 15, 2009, Mar. 3, 2010 and Aug. 19, 2010).

U.S. Appl. No. 10/638,562 of Binette et al. (see Office Actions dated Dec. 9, 2005, Aug. 23, 2006, Nov. 9, 2006, Jan. 11, 2007, Jul. 9, 2007, Sep. 26, 2007, Jan. 11, 2008, Oct. 9, 2008, Jan. 28, 2009, Jun. 19, 2009, Jan. 15, 2010, and Apr. 22, 2010).

U.S. Appl. No. 11/947,384 of Binette et al.

U.S. Appl. No. 10/458,615 of Melican et al., now abandoned (see Office Actions dated Sep. 27, 2005, Feb. 22, 2006, May 31, 2006, Nov. 27, 2006, and May 30, 2007)

Defrere et al., "Teflon/polyurethane arthroplasty of the knee: the first 2 years preliminary clinical experience in a new concept of artificial resurfacing of full thickness cartilage legions of the knee," Acta Chir. Belg., 1992, vol. 92, No. 5, pp. 217-227.

Dialog English language abstract for DE 19812195, published Sep. 30, 1999.

Examination file history of EP 01310810, priority date of Dec. 21, 2000. (Note: 444 pages).

European Search Report for EP 10075307 mailed Oct. 6, 2010.

Japanese Office Action, from JP 2004-191861, mailed Mar. 1, 2011.

Andreasen, J.O. et al. Evaluation of different types of autotransplanted connective tissues as potential periodontal ligament substitues: An experimental replantation study in monkeys, International Journal of Oral Surgery, Jun. 1981, vol. 10, Issue 3, pp. 189-201.

Japanese Office Action from JP 2004-233655, mailed Dec. 6, 2011.

* cited by examiner

Percent Fill: Good (68%)

NONWOVEN TISSUE SCAFFOLD

BACKGROUND OF THE INVENTION

The present invention generally relates to methods and apparatus for repairing meniscal defects, and in particular to tissue repair scaffold devices having enhanced properties.

The meniscus is specialized tissue found between the bones of a joint. For example, in the knee the meniscus is a C-shaped piece of fibrocartilage which is located at the peripheral aspect of the joint between the tibia and femur. This tissue performs important functions in joint health including adding joint stability, providing shock absorption, and delivering lubrication and nutrition to the joint. As a result, meniscal injuries can lead to debilitating conditions such as degenerative arthritis.

Meniscal injuries, and in particular tears, are a relatively common injury. Such injuries can result from a sudden twisting-type injury such as a fall, overexertion during a work-related activity, during the course of an athletic event, or in any one of many other situations and/or activities. In addition, tears can develop gradually with age. In either case, the tears can occur in either the outer thick part of the meniscus or through the inner thin part. While some tears may involve only a small portion of the meniscus, others affect nearly the entire meniscus.

Unfortunately, a damaged meniscus is unable to undergo the normal healing process that occurs in other parts of the body. The peripheral rim of the meniscus at the menisco-synovial junction is highly vascular (red zone) whereas the inner two-thirds portion of the meniscus is completely avascular (white zone), with a small transition (red-white zone) between the two. Degenerative or traumatic tears to the meniscus which result in partial or complete loss of function frequently occur in the white zone where the tissue has little potential for regeneration. Such tears result in severe joint pain and locking, and in the long term, a loss of meniscal function leading to osteoarthritis.

Although several treatments currently exist for meniscal injuries, the treatment options provide little opportunity for meniscal repair or regeneration. The majority of meniscal injuries are treated by removing the unstable tissue during a partial meniscectomy. Once the tissue is removed no further treatment is conducted. Most patients respond well to this treatment in the short term but often develop degenerative joint disease several years (i.e., after more than about 10 years) post operatively. The amount of tissue removed has been linked to the extent and speed of degeneration. When the majority of the meniscal tissue is involved in the injury, a total meniscectomy is conducted. If the patient experiences pain after a total meniscectomy without significant joint degeneration, a secondary treatment of meniscal allografts is possible. The use of allografts is limited by tissue availability and by narrow indications.

For meniscal tears that can be stabilized in vascularized areas of the meniscus, the tears can be repaired with suture or equivalent meniscal repair devices such as RapidLoc (DePuy Mitek) and FasT Fix (Smith & Nephew). While these repairs are successful in approximately 60-80% of the cases, the percentage of injuries which meet the criteria to be repaired is 15% or less. Repair criteria are based not only on vascularity and type of tear but also stability and integrity of the meniscus, stability of the knee and patient factors such as age and activity. If the repair does fail, the next possible course of treatment is either a partial or total meniscectomy.

Despite existing technology, there continues to exist a need in this art for novel tissue repair devices capable of encouraging meniscal tissue regeneration, as well as methods for using such tissue repair devices.

SUMMARY OF THE INVENTION

The present invention provides a biocompatible meniscal repair device comprising a biocompatible tissue repair scaffold adapted to be placed in contact with a defect in a meniscus. The scaffold is formed from a nonwoven material, and the scaffold can additionally include a foam component. In one aspect, the material is a high density nonwoven.

Preferably, the nonwoven material of the scaffold of the present invention is formed from one or more biocompatible polymers including at least one polymer derived from monomer(s) selected from the group consisting of glycolide, lactide, caprolactone, trimethylene carbonate, polyvinyl alcohol, and dioxanone. In one embodiment, the scaffold is comprised of bioabsorbable polymers.

The nonwoven material from which the scaffold is formed comprises materials formed by a dry lay process using synthetic polymer fibers. Preferably, the nonwoven is produced by processing continuous filament yarn into crimped yarn, which is then cut into staple fiber of uniform length. The staple fiber is then preferably carded into a batt or web which is needle-punched. Even more preferably, the resulting nonwoven has an isotropic fiber orientation.

The nonwoven material that forms the scaffold preferably has desirable material properties that enhance its efficacy as a meniscal repair device. In one aspect of the invention, the nonwoven material of the scaffold has a modulus of elasticity greater than about 0.1 MPA, and even more preferably greater than about 1.5 MPa, a suture pull-out strength greater than about 6 N, and/or a peak stress greater than about 0.2 MPa, and even more preferably greater than 2 MPa. The preferred ranges of these properties include a modulus of elasticity in the range of about 2 MPa to 40 MPa; a suture pull-out strength in the range of about 6 N to 45 N; and a peak stress in the range of about 2 MPa to 14 MPa. In addition, the thickness of the scaffold is preferably in the range of about 0.5 mm to 1.5 mm.

In another aspect of the invention, the repair device further comprises at least one bioactive substance effective to stimulate cell growth. Preferably the bioactive substance is selected from the group consisting of a platelet rich plasma, cartilage-derived morphogenic proteins, recombinant human growth factors, and combinations thereof. In another embodiment the repair device includes a viable tissue sample disposed on the tissue repair scaffold and effective to integrate with native tissue adjacent to the tissue repair scaffold.

BRIEF DESCRIPTION OF THE DRAWINGS

The invention will be more fully understood from the following detailed description taken in conjunction with the accompanying drawings, in which:

FIG. 22 is another photomicrograph of the Group 1 results from Example 4; and

DETAILED DESCRIPTION OF THE INVENTION

Figure 1A:
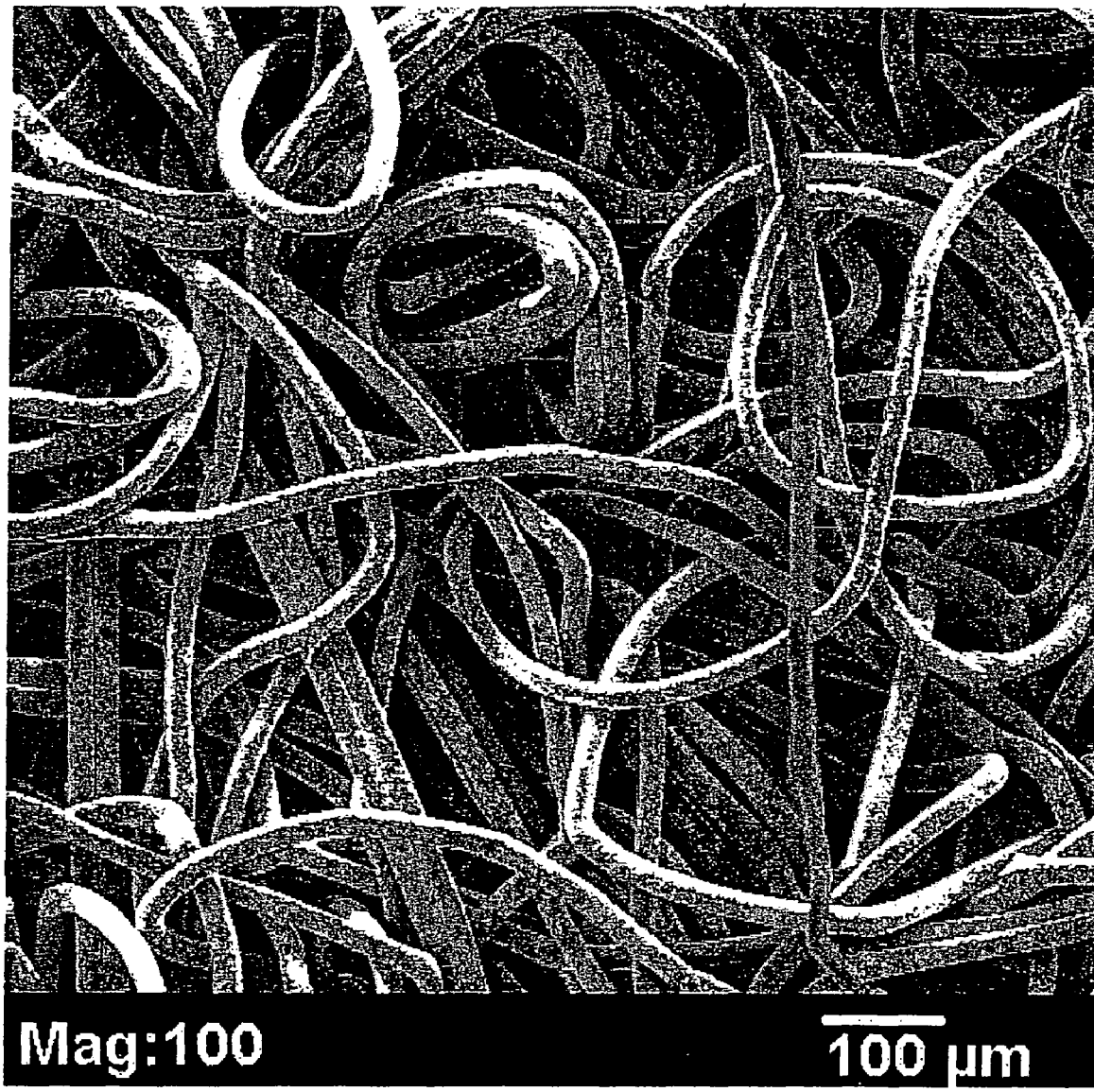
FIG. 1A is a photomicrograph (100×) of a tissue repair device constructed according to the present invention.

The present invention provides a meniscal repair device having a biocompatible tissue repair scaffold adapted to be placed in contact with a defect in a meniscus. The scaffold comprises a high-density, nonwoven polymeric material with advantageous mechanical characteristics, preferably including a modulus of elasticity greater than about 1.5 MPa, a peak stress greater than about 2 MPa, and a suture retention strength greater than about 6 N. The scaffold may additionally include a biocompatible foam.

The small size of meniscal defects, such as meniscal tears, require similarly small repair devices for positioning in or adjacent to the tissue defect. Unfortunately, many of the materials used to construct conventional devices to repair such defects lack the required strength to withstand the stresses to which the knee joint is subjected while allowing the repair devices to remain intact within the meniscal tissue. As a result, many attempts to treat meniscal defects have failed because the implanted devices migrate from the defect site or unravel after implantation. The present invention overcomes these drawbacks and provides a scaffold sized for meniscal repair, and which possesses physical properties sufficient to resist tearing and unwanted degradation.

The repair device of the present invention includes a scaffold comprising a nonwoven material. Preferred nonwoven materials include flexible, porous structures produced by interlocking layers or networks of fibers, filaments, or film-like filamentary structures. Such nonwoven materials can be formed from webs of previously prepared/formed fibers, filaments, or films processed into arranged networks of a desired structure.

Generally, nonwoven materials are formed by depositing the constituent components (usually fibers) on a forming or conveying surface. These constituents may be in a dry, wet, quenched, or molten state. Thus, the nonwoven can be in the form of a dry laid, wet laid, or extrusion-based material, or hybrids of these types of nonwovens can be formed. The fibers or other materials from which the nonwovens can be made are typically polymers, either synthetic or naturally occurring.

Those having skill in the art will recognize that dry laid scaffolds include those nonwovens formed by garneting, carding, and/or aerodynamically manipulating dry fibers in the dry state. In addition, wet laid nonwovens are well known to be formed from a fiber-containing slurry that is deposited on a surface, such as a moving conveyor. The nonwoven web is formed after removing the aqueous component and drying the fibers. Extrusion-based nonwovens include those formed from spun bond fibers, melt blown fibers, and porous film systems. Hybrids of these nonwovens can be formed by combining one or more layers of different types of nonwovens by a variety of lamination techniques.

The term "nonwoven" as used in the present invention, and as understood by one skilled in the art, does not include woven, knit, or mesh fabrics. In addition, the nonwovens of the present invention preferably have a density designed to obtain mechanical characteristics ideal for augmenting meniscal repair. In one embodiment, the density of the nonwoven is in the range of about 120 mg/cc to 360 mg/cc.

The scaffold of the present invention is preferably formed from a biocompatible polymer. A variety of biocompatible polymers can be used to form the biocompatible nonwoven and/or biocompatible foam according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring.

In embodiments where the scaffold includes at least one synthetic polymer, suitable biocompatible synthetic polymers can include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof. Suitable synthetic polymers for use in the present invention can also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-, L-and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Other useful polymers include polyphosphazenes, co-, ter-and higher order mixed monomer based polymers made from L-lactide, D,L-lactide, lactic acid, glycolide, glycolic acid, para-dioxanone, trimethylene carbonate and ε-caprolactone.

In embodiments where the scaffold includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of non-limiting example, the biocompatible scaffold can included a collagen-based small intestine submucosa.

One skilled in the art will appreciate that the selection of a suitable material for forming the biocompatible scaffold of the present invention depends on several factors. These factors include in vivo mechanical performance; cell response to the material in terms of cell attachment, proliferation, migration and differentiation; biocompatibility; and optionally, bioabsorption (or bio-degradation) kinetics. Other relevant factors include the chemical composition, spatial distribution of the constituents, the molecular weight of the polymer, and the degree of crystallinity.

Figure 1B:
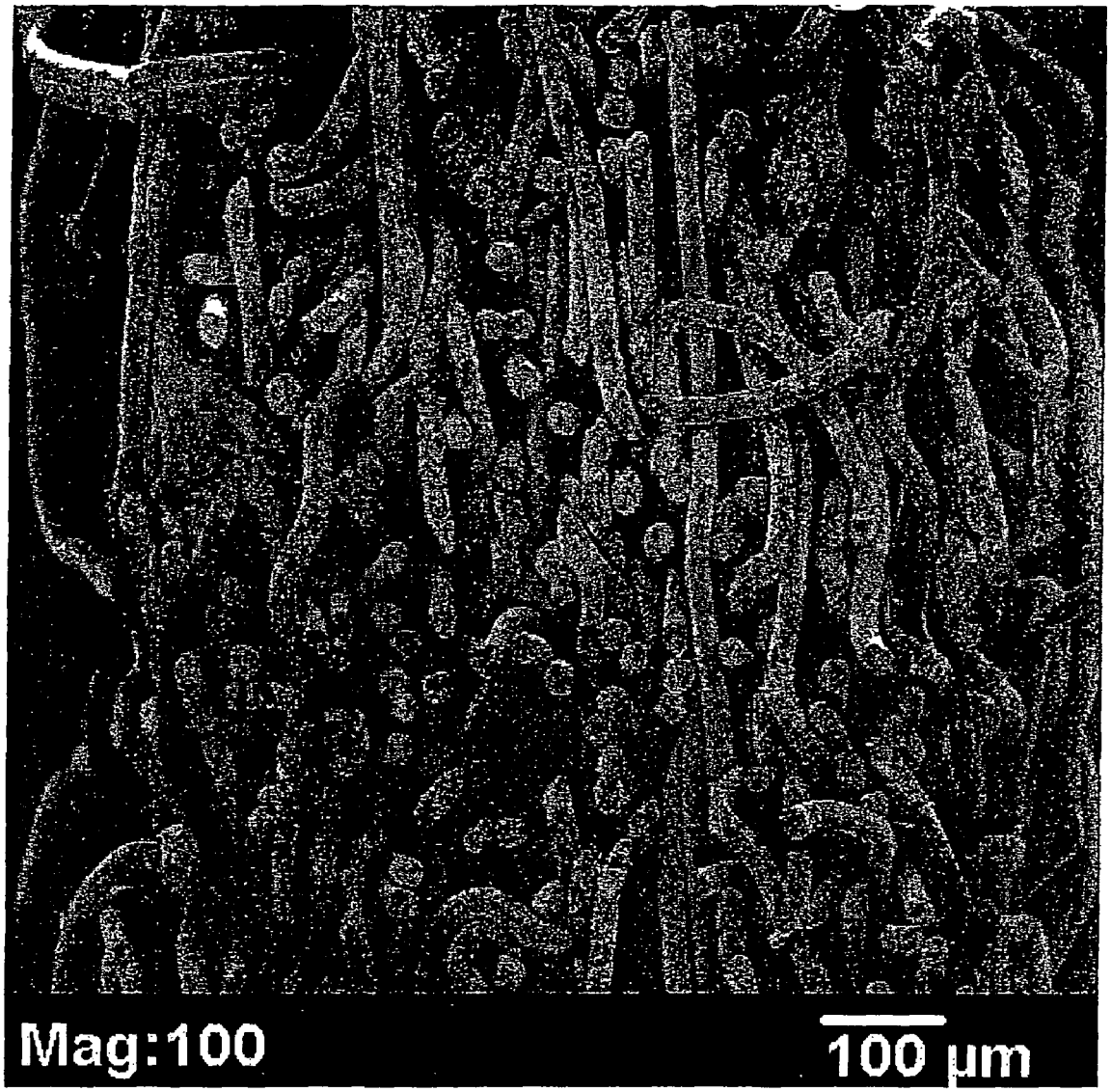
FIG. 1B is a photomicrograph cross sectional view (100×) of the tissue repair device shown in FIG. 1A.
Figure 2A:
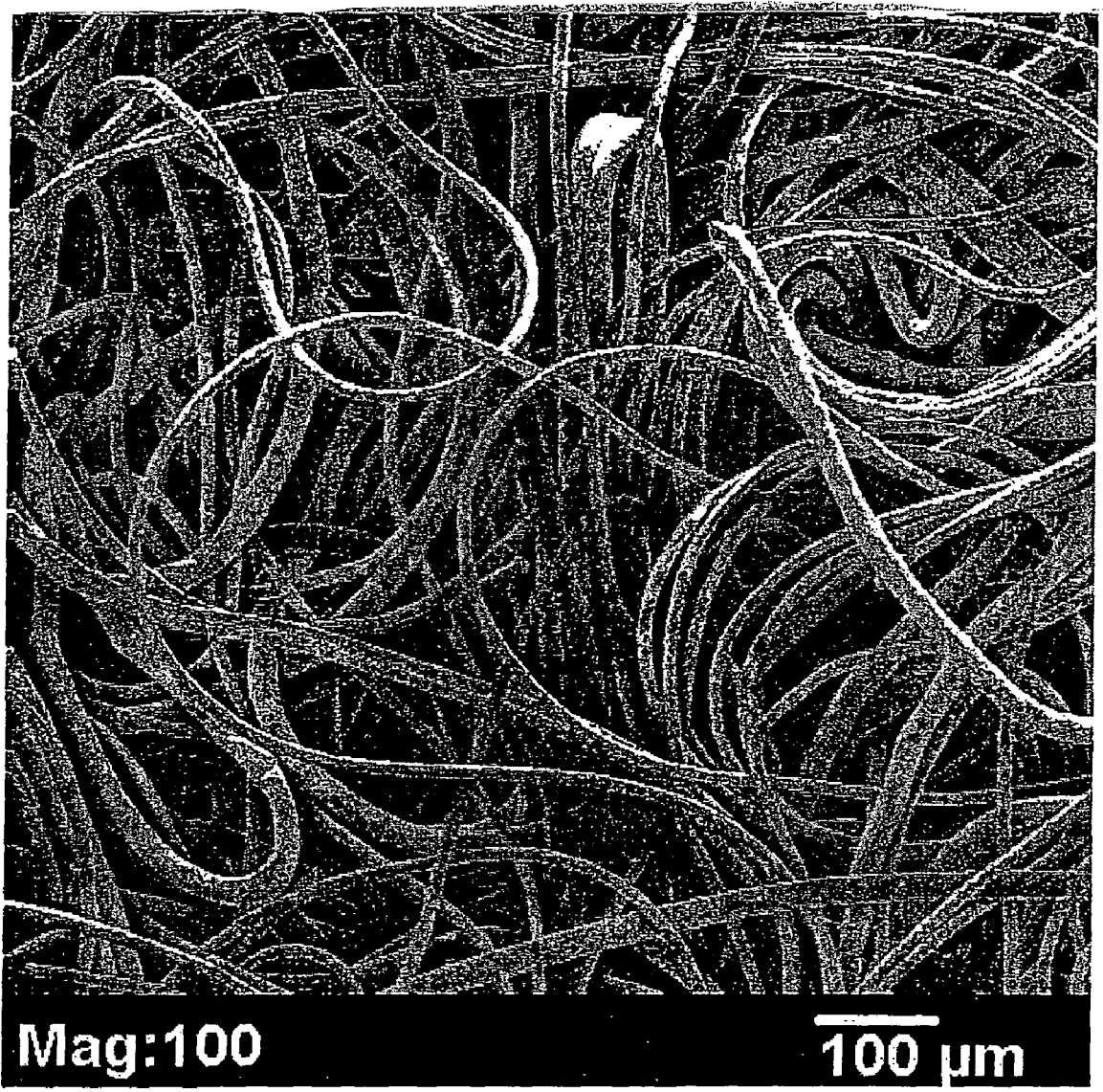
FIG. 2A is photomicrograph top view (100×) of an alternative embodiment of the tissue repair device constructed according to the present invention.
Figure 2B:
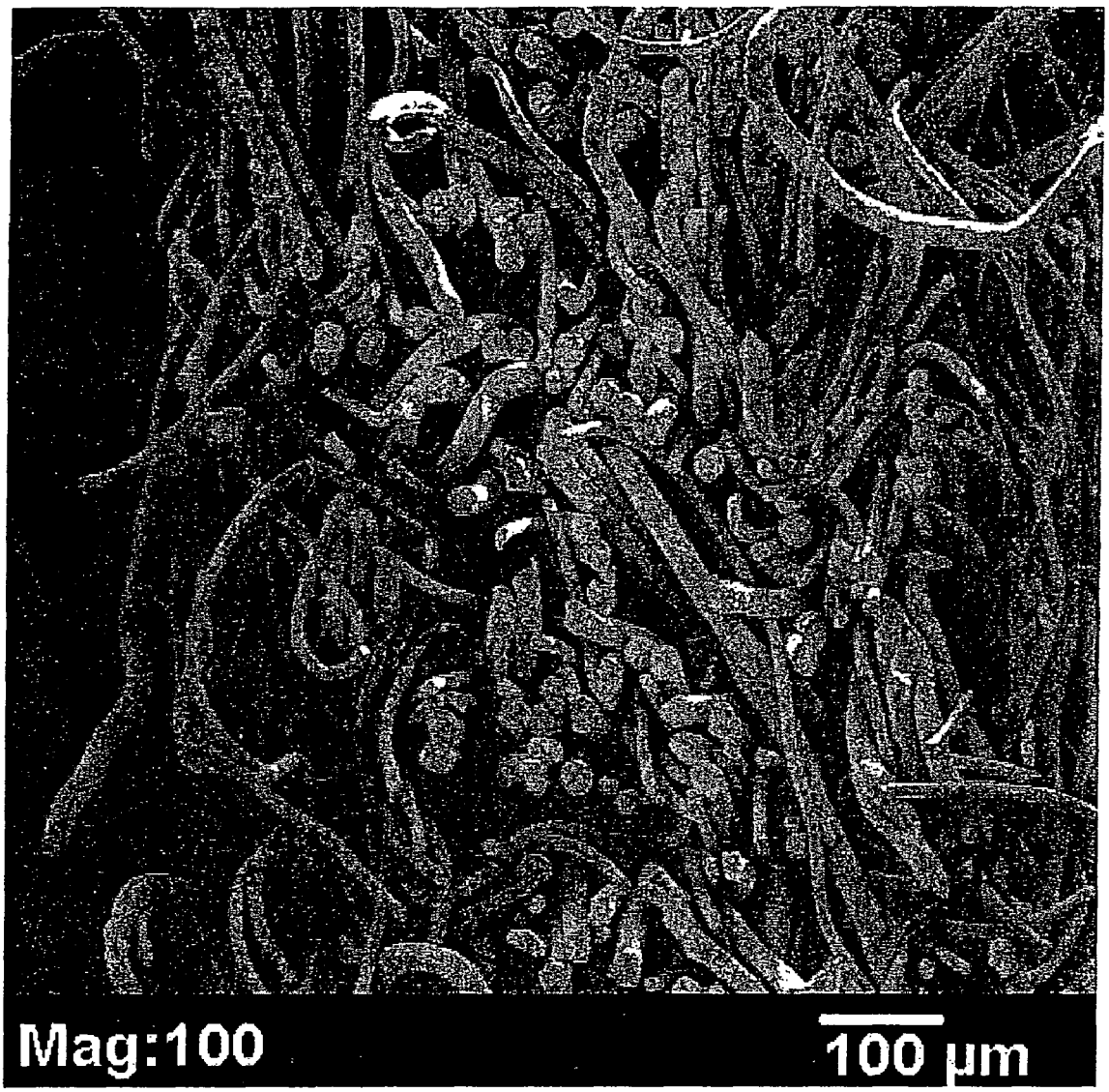
FIG. 2B is photomicrograph cross sectional view (100×) of the tissue repair device shown in FIG. 2A.

FIGS. 1A and 1B illustrate Scanning Electron Micrographs of an exemplary nonwoven scaffold useful as the repair device of the present invention. FIG. 1A is top view of a polydioxanone ("PDS") nonwoven with a density of 275.5 mg/cc, while FIG. 1B shows a cross sectional view of the same nonwoven. FIGS. 2A and 2B, respectively, illustrate a top view and a cross sectional view of another exemplary nonwoven comprising a 50/50 PDS/VICRYL ("VICRYL" is a copolymer of polyglycolic acid and polylactic acid) polymer having a density of 236.6 mg/cc.

In one embodiment, the scaffold of the present invention includes a biocompatible foam component mated with the nonwoven material. In one aspect, the foam material is formed as a layer on one or both sides of a layer of nonwoven material. Alternatively, the foam material and the nonwoven material can be interlocked such that the foam component is integrated within the nonwoven material and the pores of the foam component penetrate the nonwoven material and interlock with the nonwoven component. Preferred foam materials include those with an open cell pore structure.

Figure 3A:
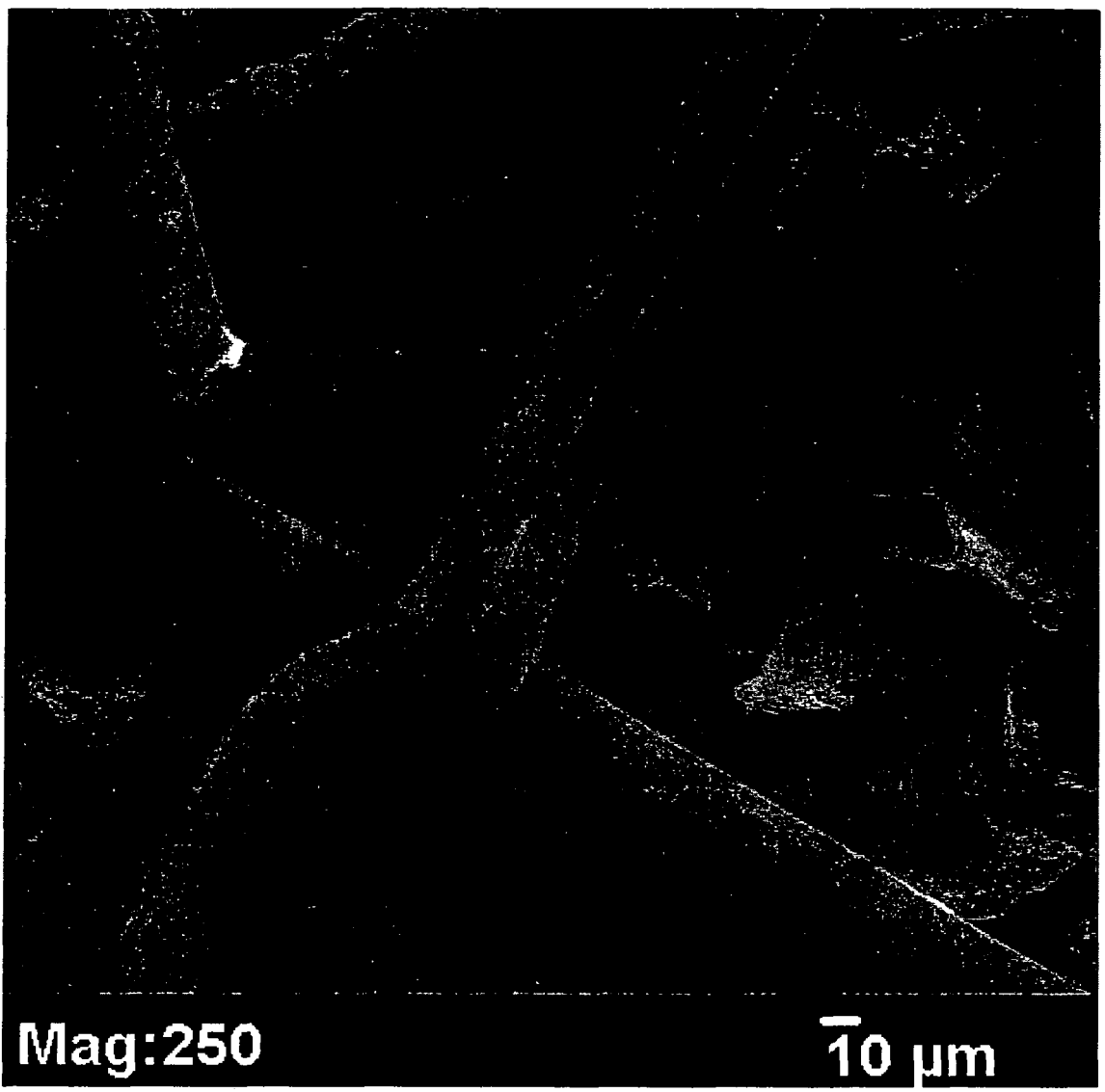
FIG. 3A is a photomicrograph top view (25×) of yet another embodiment of the tissue repair device of the present invention.
Figure 3B:
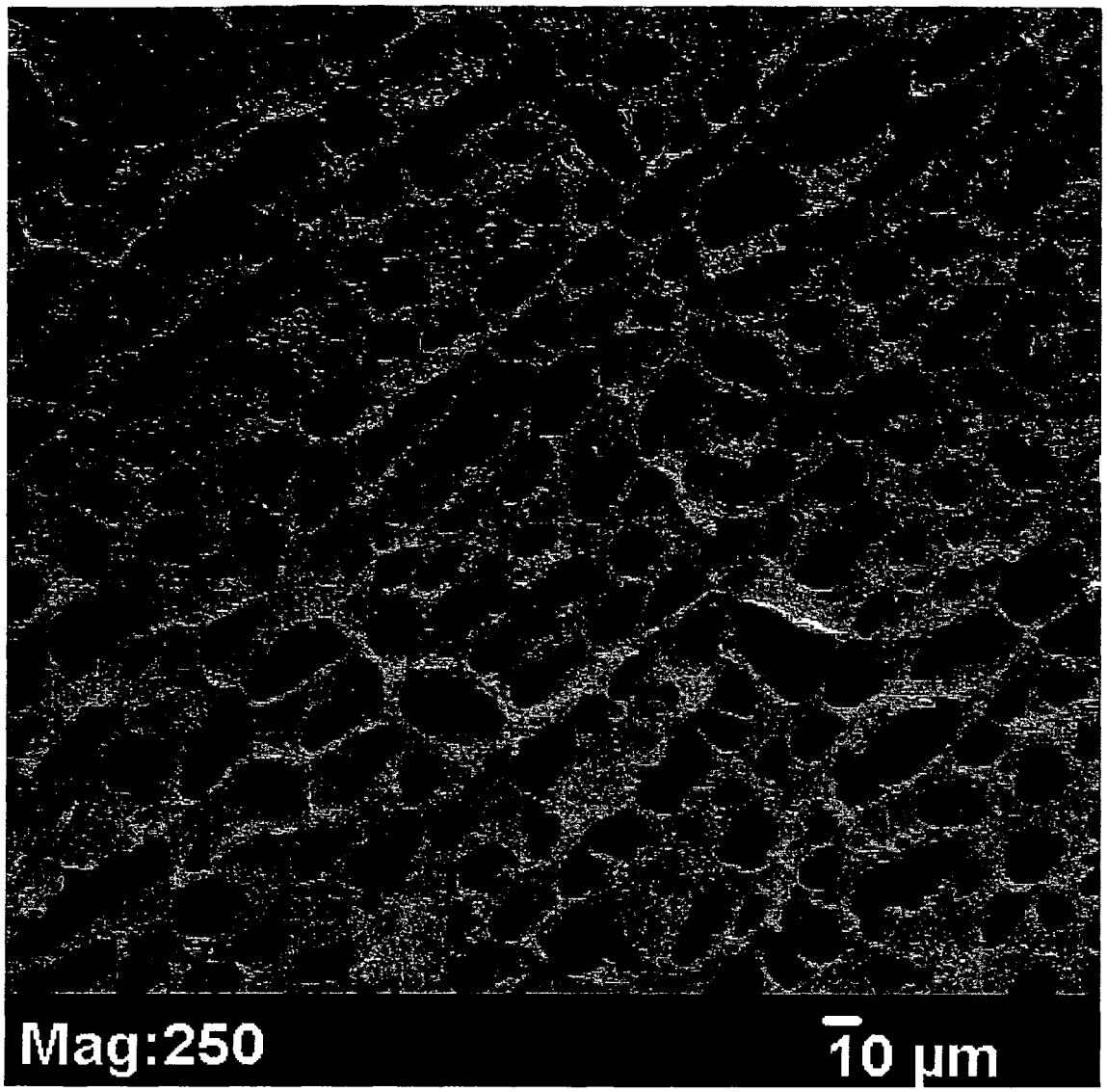
FIG. 3B is a photomicrograph bottom view (25×) of the tissue repair device shown in FIG. 3A.
Figure 3C:
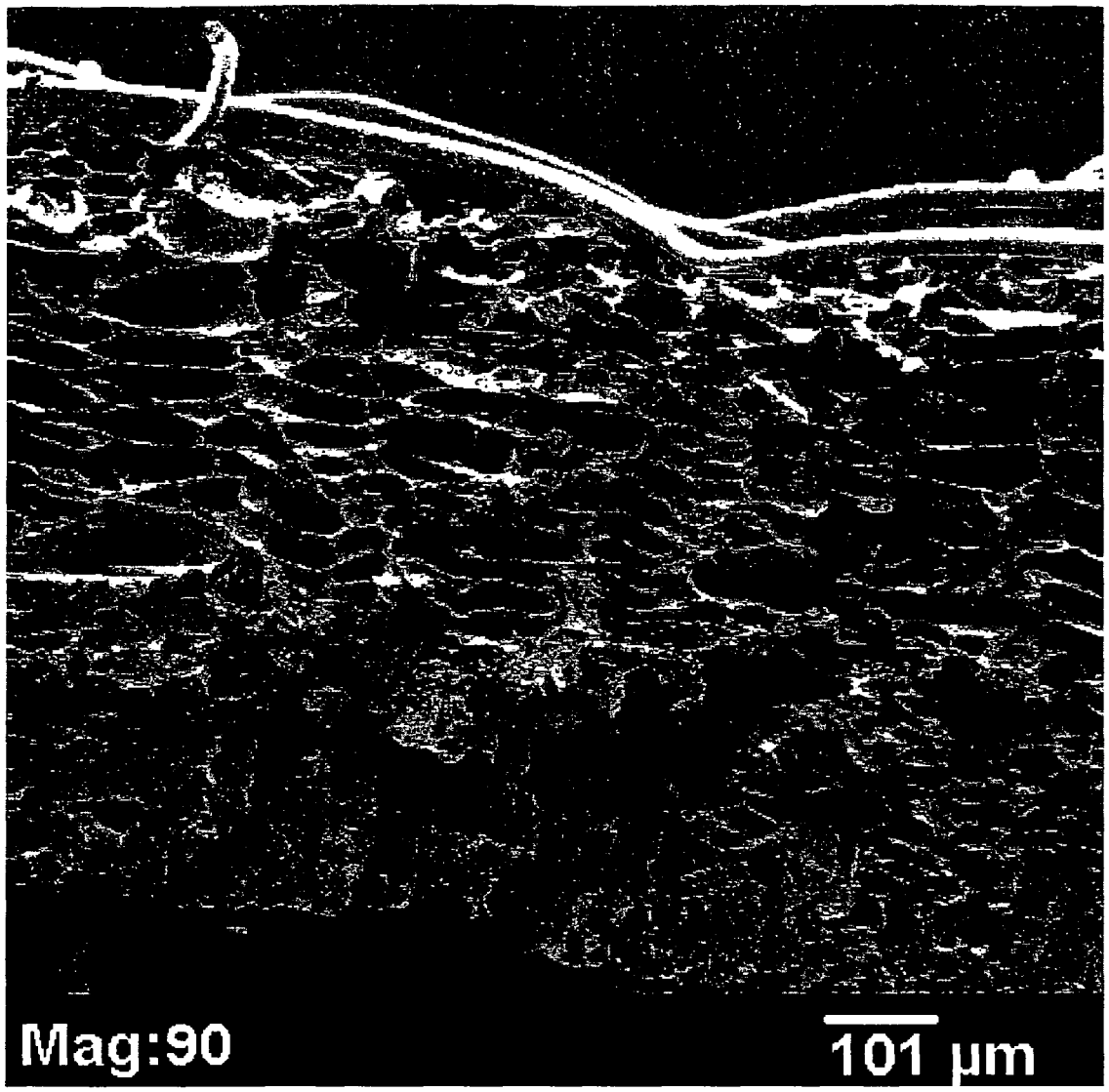
FIG. 3C is a photomicrograph cross sectional view (90×) of the tissue repair device shown in FIG. 3A.
Figure 3D:
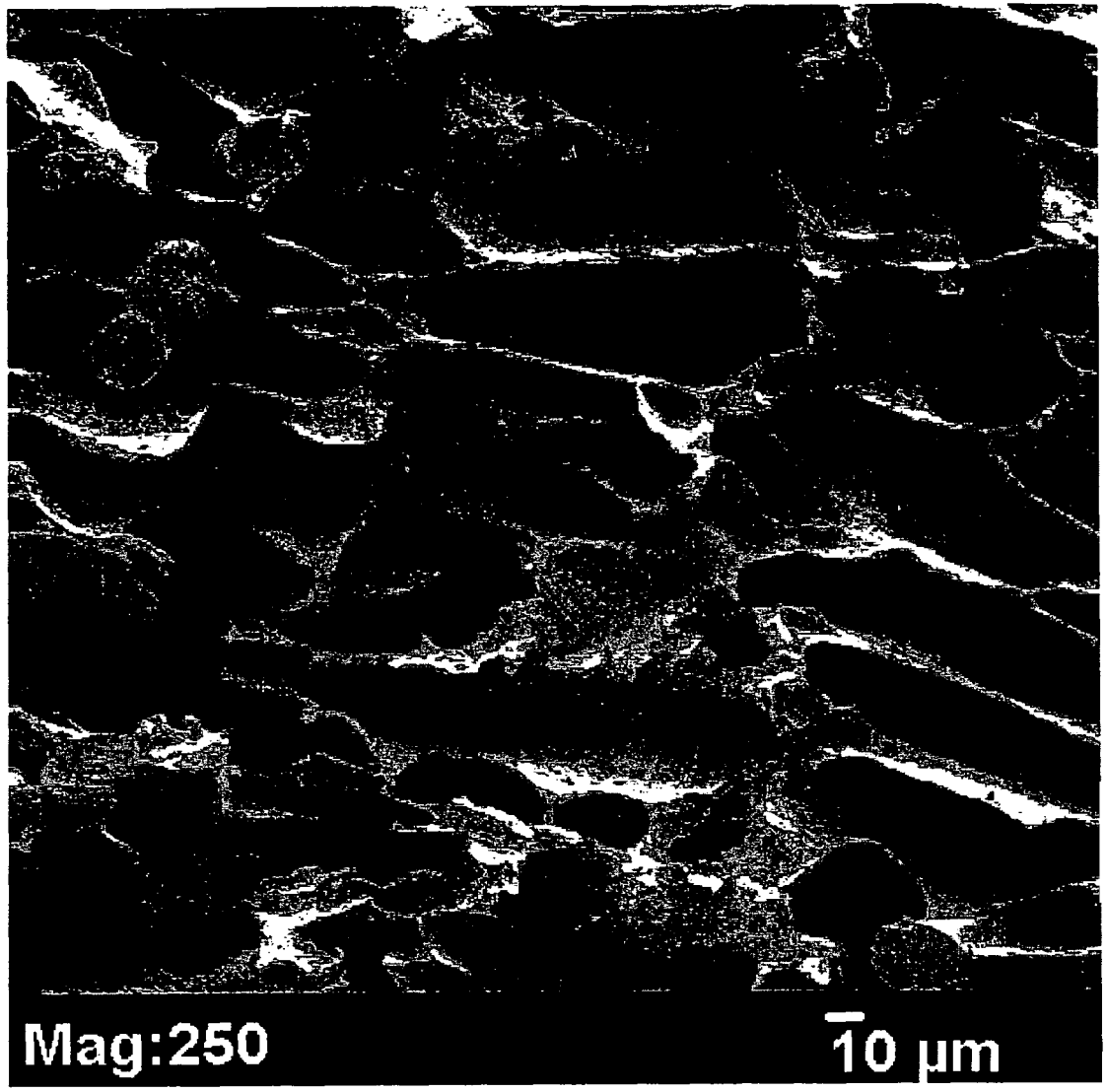
FIG. 3D is yet another photomicrograph cross sectional view (25×) of the tissue repair device shown in FIG. 3A.

FIGS. 3A-3D illustrate a composite foam/nonwoven scaffold comprising a PDS nonwoven with a density of 240 mg/cc and a 65/35 polyglycolic acid ("PGA")/polycaprolactone ("PCL") foam interlocked therewith. FIGS. 3A and 3B show top and bottom views, respectively. FIGS. 3C and 3D show cross sectional views at a magnification of 90 and 250, respectfully. As demonstrated by the cross sectional views, the fibers of the nonwoven material extend through the foam and interlock with the foam.

In one embodiment of the present invention, the foam material includes elastomeric copolymers such as, for example, polymers having an inherent viscosity in the range of about 1.2 dL/g to 4 dL/g, more preferably about 1.2 dL/g to 2 dL/g, and most preferably about 1.4 dL/g to 2 dL/g as determined at 25° C. in a 0.1 gram per deciliter (g/dL) solution of polymer in hexafluoroisopropanol (HFIP). Suitable elastomers also preferably exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, the elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers include, but are not limited to, elastomeric copolymers of ε-caprolactone and glycolide with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 95:5 to about 30:70 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Other examples of suitable biocompatible elastomers are described in U.S. Pat. No. 5,468,253.

The biocompatible foam material may also include thin elastomeric sheets with pores or perforations to allow tissue ingrowth. Such a sheet could be made of blends or copolymers of polylactic acid (PLA), polyglycolic acid (PGA), polycaprolactone (PCL), and polydioxanone (PDS).

In another embodiment, the foam component comprises an elastomer that is a copolymer of 35:65 ε-caprolactone and glycolide. In yet another embodiment, the foam used in the tissue scaffold can be a copolymer of 40:60 ε-caprolactone and lactide. In yet a further embodiment, the foam component is a 50:50 blend of a 35:65 copolymer of ε-caprolactone and glycolide and 40:60 copolymer of ε-caprolactone and lactide.

It may also be desirable to use polymer blends which transition from one composition to another composition in a gradient-like architecture. Scaffolds having this gradient-like architecture are particularly advantageous in tissue engineering applications to repair or regenerate the structure of naturally occurring tissue such as cartilage. For example, by blending an elastomer of ε-caprolactone-co-glycolide with ε-caprolactone-co-lactide (e.g., with a mole ratio of about 5:95) a scaffold may be formed that transitions from a softer spongy material to a stiffer more rigid material, for example, in a manner similar to the transition from cartilage to bone. Clearly, one skilled in the art will appreciate that other polymer blends may be used to adjust the gradient effects, or to provide different gradients (e.g., different absorption profiles, stress response profiles, or different degrees of elasticity).

As noted above, the scaffold of present invention has a number of desirable properties. In one embodiment, the device of the present invention has a suture pull-out strength greater than 6 N, and preferably in the range of about 6 N to 45 N. The scaffold also preferably has a modulus of elasticity greater than 0.1 MPa, and more preferably greater than 2.0 MPa, and in one embodiment is in the range of about 2 MPa to 40 MPa. Other desirable properties of the scaffold include peak stress and stiffness. Preferably, the peak stress is greater than 0.2 MPa, and even more preferably greater than 2 MPA, and in one embodiment is in the range of about 2 MPa to 14 MPa. The stiffness of the scaffold is preferably greater than 0.5 N/mm. Compared to conventional meniscal implant devices, these properties render the scaffold of the present invention better suited to the demanding conditions within the knee joint and can be fixed in place with less risk of the implant migrating or unraveling.

The nonwoven material of the present invention can also include a variety of fibers such as monofilaments, yarns, threads, braids, bundles or combinations thereof. The fibers can be constructed from any of the biocompatible material described above, such as, for example bioabsorbable materials such as polylactic acid (PLA), polyglycolic acid (PGA), polycaprolactone (PCL), polydioxanone (PDS), trimethylene carbonate (TMC), copolymers or blends thereof. These fibers can also be made from any biocompatible materials based on natural polymers including silk and collagen-based materials. These fibers can also be made of any biocompatible fiber that is nonresorbable, such as, for example, polyethylene, polyethylene terephthalate, poly(tetrafluoroethylene), polycarbonate, polypropylene and poly(vinyl alcohol). In one preferred embodiment, the fibers are formed from polydioxanone.

In another embodiment, the described biocompatible polymers are used to form a polymeric foam component having pores with an open cell pore structure. The pore size can vary, but preferably, the pores are sized to allow tissue ingrowth. More preferably, the pore size is in the range of about 25 to 1000 microns, and even more preferably, in the range of about 50 to 500 microns.

A viable tissue can also be included in the scaffold of the present invention. The source can vary and the tissue can have a variety of configurations, however, in one embodiment the tissue is in the form of finely minced tissue fragments, which enhance the effectiveness of tissue regrowth and encourage a healing response. In another embodiment, the viable tissue can be in the form of a tissue slice or strip harvested from healthy tissue that contains viable cells capable of tissue regeneration and/or remodeling.

Suitable tissue that can be used to obtain viable tissue includes, for example, cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood, and combinations thereof. The tissue used to construct the tissue implant can be autogeneic tissue, allogeneic tissue, or xenogeneic tissue. In a preferred embodiment, the viable tissue is meniscal tissue.

The viable tissue can also optionally be combined with a variety of other materials, including carriers, such as a gel-like carrier or an adhesive. By way of non-limiting example, the gel-like carrier can be a biological or synthetic hydrogel such as hyaluronic acid, fibrin glue, fibrin clot, collagen gel, collagen-based adhesive, alginate gel, crosslinked alginate, chitosan, synthetic acrylate-based gels, platelet rich plasma (PRP), platelet poor plasma (PPP), PRP clot, PPP clot, blood, blood clot, blood component, blood component clot, Matrigel, agarose, chitin, chitosan, polysaccharides, poly(oxyalkylene), a copolymer of poly(ethylene oxide)-poly(propylene oxide), poly(vinyl alcohol), laminin, elasti, proteoglycans, solubilized basement membrane, or combinations thereof. Suitable adhesives include, but are not limited to, hyaluronic acid, fibrin glue, fibrin clot, collagen gel, collagen-based adhesive, alginate gel, crosslinked alginate, gelatin-resorcin-formalin-based adhesive, mussel-based adhesive, dihydroxyphenylalanine (DOPA)-based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), PRP clot, PPP clot, blood, blood clot, blood component, blood component clot, polyethylene glycol-based adhesive, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

The viable tissue can also be contacted with a matrix-digesting enzyme to facilitate tissue migration out of the extracellular matrix surrounding the viable tissue. The enzymes can be used to increase the rate of cell migration out of the extracellular matrix and into the tissue defect or injury, or scaffold material. Suitable matrix-digesting enzymes that can be used in the present invention include, but are not limited to, collagenase, chondroitinase, trypsin, elastase, hyaluronidase, peptidase, thermolysin, matrix metalloproteinase, gelatinase and protease. Preferably, the concentration of minced tissue particles in the gel-carrier is in the range of approximately 1 to 1000 mg/cm$^3$, and more preferably in the range of about 1 to 200 mg/cm$^3$.

In another embodiment of the present invention, a bioactive agent may be incorporated within and/or applied to the tissue scaffolds, and/or it can be applied to the viable tissue. Preferably, the bioactive agent is incorporated within, or coated on, the scaffold prior to the addition of viable tissue to the scaffold. The bioactive agent(s) can be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED® and SURGICEL®, available from Ethicon, Inc.), hyaluronic acid, and compounds or agents that suppress the immune system (e.g., immunosuppressants).

By way of non-limiting example, other types of effectors present within the implant of the present invention can include heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the scaffold, or alternatively, the scaffold can include a source of growth factors, such as for example, platelets. "Bioactive agents," as used herein, can include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short term peptides, bone morphogenic proteins, glycoprotein and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGF-$\beta$ I-III), parathyroid hormone, parathyroid hormone related peptide, bone morphogenic proteins (e.g., BMP-2, BMP-4; BMP-6; BMP-12), sonic hedgehog, growth differentiation factors (e.g., GDF5, GDF6, GDF8), recombinant human growth factors (e.g., MP52), cartilage-derived morphogenic proteins (CDMP-1)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopaedic field, it is anticipated that at least some of these substances will have use in the present invention, and such substances should be included in the meaning of "bioactive agent" and "bioactive agents" unless expressly limited otherwise.

Biologically derived agents, suitable for use as effectors, include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also appropriate biologically derived agents. If other such substances have therapeutic value in the orthopaedic field, it is anticipated that at least some of these substances will have use in the present invention, and such substances should be included in the meaning of "biologically derived agent" and "biologically derived agents" unless expressly limited otherwise.

Biologically derived agents also include bioremodelable collageneous tissue matrices. The terms "bioremodelable collageneous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, whatever the source. Although the term "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one skilled in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The tissue scaffolds of the present invention can also have cells incorporated therein. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited.

Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The tissue scaffold of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the biocompatible scaffold of the tissue repair device, the device can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One skilled in the art will appreciate that the identity of the bioactive agent may be determined by a surgeon, based on principles of medical science and the applicable treatment objectives. It is also understood that the bioactive agent or effector of the tissue repair device can be incorporated within the tissue scaffold before, during, or after manufacture of the tissue scaffold, or before, during, or after the surgical placement of the device.

Prior to surgical placement, the tissue scaffold can be placed in a suitable container comprising the bioactive agent. After an appropriate time and under suitable conditions, the scaffold will become impregnated with the bioactive agent. Alternatively, the bioactive agent can be incorporated within the scaffold by, for example, using an appropriately gauged syringe to inject the biological agent(s) into the scaffold. In another embodiment, the bioactive agent can be incorporated in the scaffold during a lyophilization procedure. Other methods well known to those of skilled in the art can be applied in order to load a scaffold with an appropriate bioactive agent, such as mixing, pressing, spreading, centrifuging and placing the bioactive agent into the scaffold. Alternatively, the bioactive agent can be mixed with a gel-like carrier prior to injection into the scaffold.

Following surgical placement, a device wherein the biocompatible scaffold is devoid of any bioactive agent can be infused with biological agent(s), or device wherein the scaffold includes at least one bioactive agent can be augmented with a supplemental quantity of the bioactive agent. One method of incorporating a bioactive agent within a surgically installed device is by injection using an appropriately gauged syringe.

The amount of the bioactive agent included with a biocompatible scaffold will vary depending on a variety of factors, including the size of the scaffold, the material from which the scaffold is made, the porosity of the scaffold, the identity of the biologically component, and the intended purpose of the tissue repair device. One skilled in the art can readily determine the appropriate quantity of bioactive agent to include within a biocompatible scaffold for a given application in order to facilitate and/or expedite the healing of tissue. The amount of bioactive agent will, of course, vary depending upon the identity of the bioactive agent and the given application.

The following non-limiting examples are illustrative of the principles and practice of this invention. Numerous additional embodiments within the scope and spirit of the invention will become apparent to those skilled in the art.

EXAMPLE 1

Figure 4:
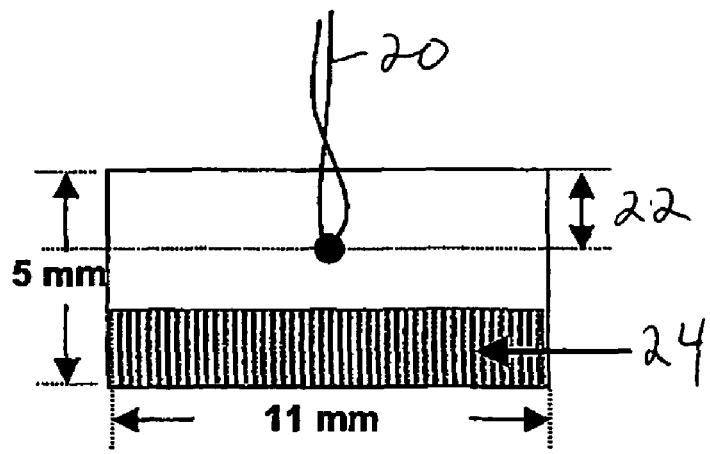
FIG. 4 is a schematic of the experimental setup for series one in Example 1.

Scaffolds made according to the present invention, as described below, were investigated and compared with conventional implants during a series of suture retention and stiffness tests. In series one, 3-0 polypropylene sutures with taper needles (Ethicon, 8665H) were placed in 5 mm×11 mm rectangles of scaffold. As shown in FIG. 4, suture 20 was given a 1.5 mm Bite-Distance 22 and a clamp 24 was positioned along the bottom portion. Half of the scaffold rectangles were mechanically tested immediately, while the remaining half were placed in DPBS (Gibco, cat# 34190-136) and incubated at 37° C. for 2 weeks before testing.

Figure 5:
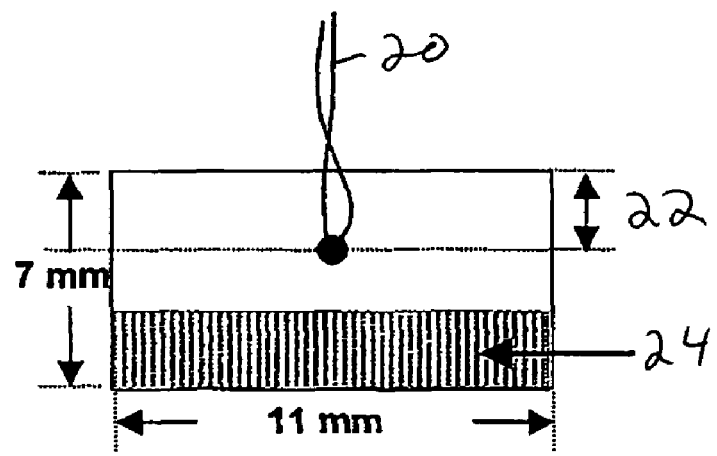
FIG. 5 is a schematic of the experimental setup for series two and three in Example 1.

In series two and three, 2-0 Ethibond sutures were placed in the 7 mm×11 mm rectangles of scaffold shown in FIG. 5. In an experimental setup similar to series one, suture 20 was positioned with a 1.5 mm Bite-Distance and clamp 24 was positioned along the bottom portion of the scaffolds. Again, half the scaffold rectangles were mechanically tested immediately, while the other half were placed in DPBS (Gibco, cat# 34190-136) and incubated at 37° C. for 2 weeks before testing.

The mechanical tests were conducted using a uniaxial Instron equipped with MTS Spring action grips (100-039-837 A). A strain rate of 5 mm/minute was applied and the force and displacement were recorded.

Figure 6A:
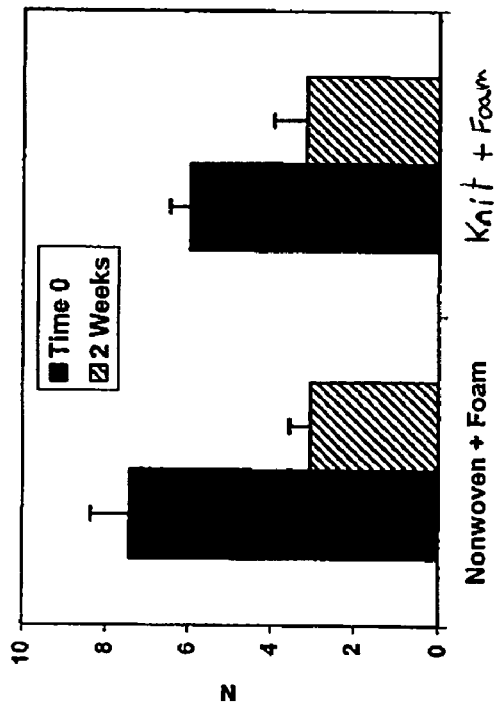
FIG. 6A is a graph illustrating the suture retention results of series one in Example 1.
Figure 6B:
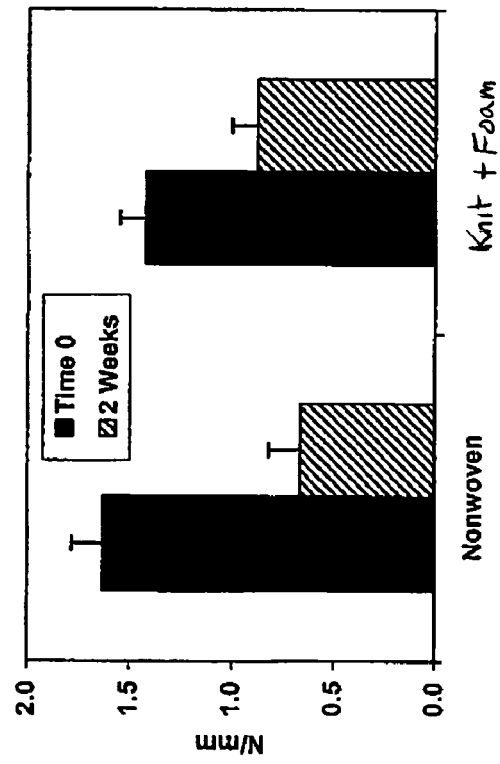
FIG. 6B is a graph illustrating the stiffness results of series one in Example 1.

In series one, the scaffold was a 65/35 PGA/PCL foam component mated with a PDS nonwoven having a density of 60 mg/cc and a thickness of 1 mm. This scaffold was compared to a conventional knit and foam implant. The results of the suture retention test are illustrated in FIGS. 6A and 6B showing the max load at suture pull-out in FIG. 6A and stiffness in FIG. 6B.

The results demonstrate that the nonwoven scaffold of the present invention has a higher suture pull-out strength than a knit and foam implant on day 0 and a similar result on day 14. The stiffness test revealed comparative results in the initial test and a small advantage for the knit/foam implant at 14 days.

Figure 7:
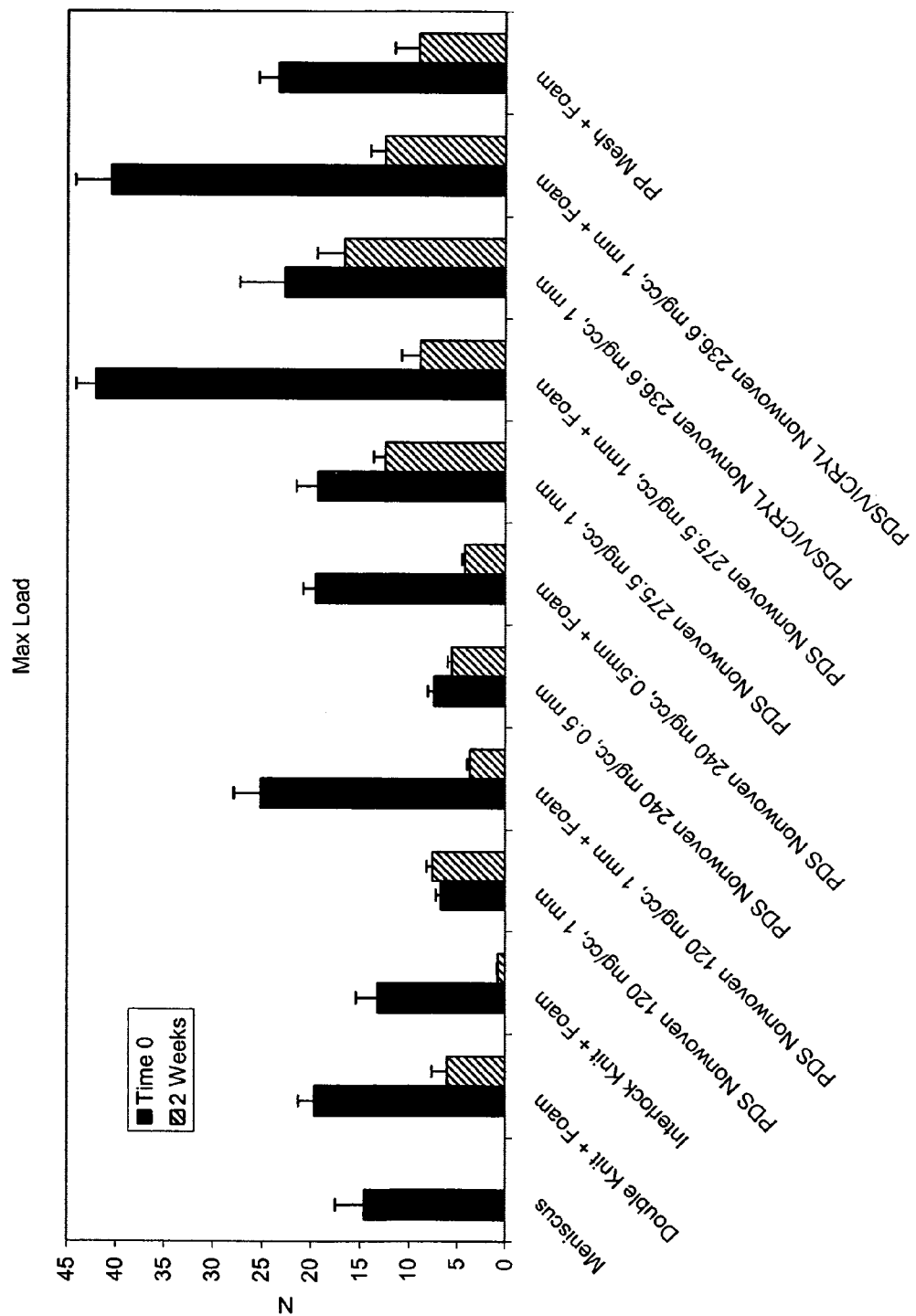
FIG. 7 is a graph illustrating the suture retention results of series two and three from Example 1.
Figure 8:
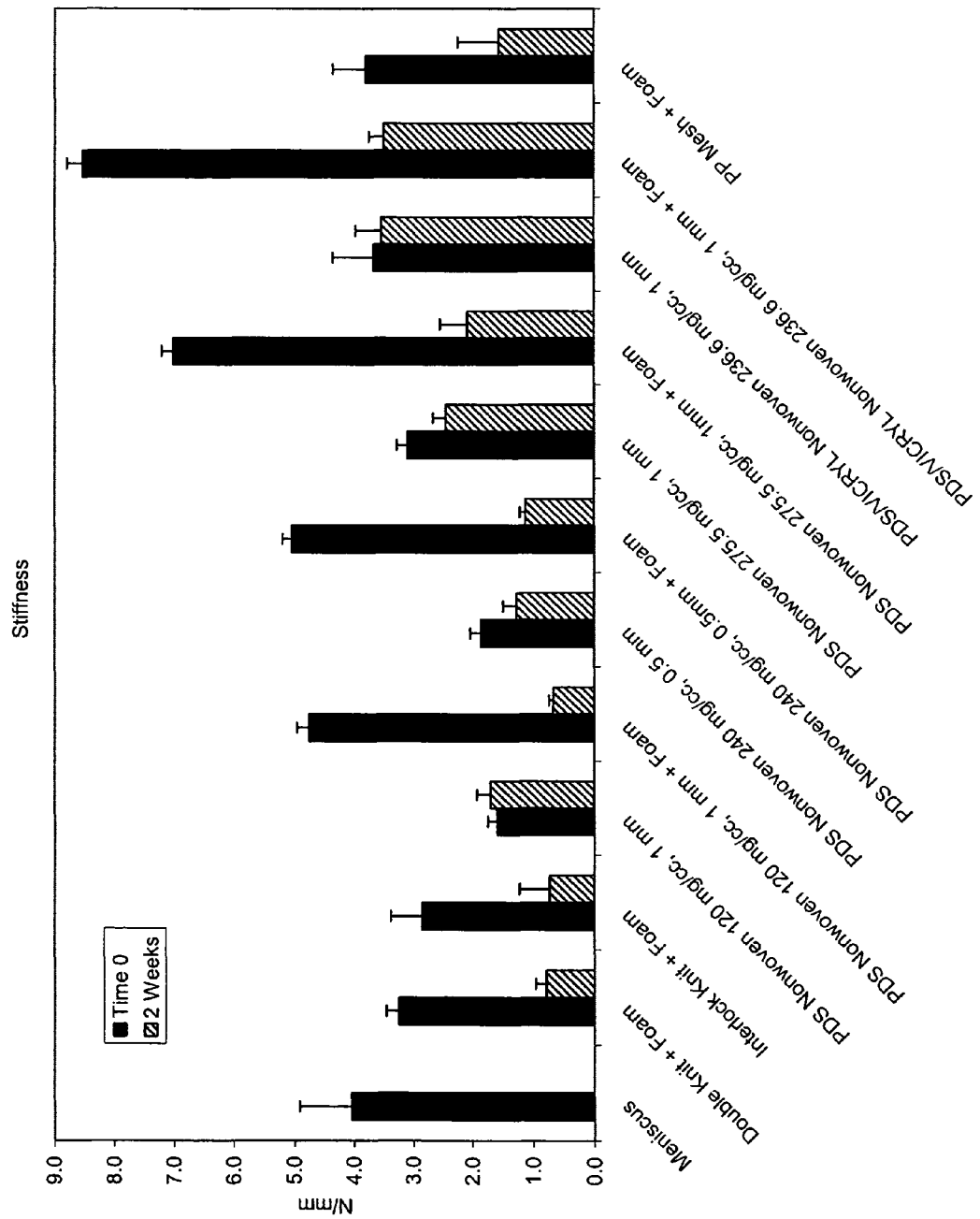
FIG. 8 is a graph illustrating the stiffness results of series two and three from Example 1.

In series two and three, twelve samples were tested, three of which were constructed with conventional materials that included a double knit with foam, a knit with foam, and a polypropylene mesh with foam. A sample of meniscal tissue was also tested. The other eight samples were repair devices constructed in accordance with the present invention from four scaffolds, each tested with and without a foam component. The four scaffolds were nonwovens that included fibers of either PDS or PDS/VICRYL and had densities of 120 mg/cc, 236.6 mg/cc, 275.5 mg/cc and 240 mg/cc. The thickness of the scaffolds was either 0.5 mm or 1 mm. The results of the suture retention test are illustrated in FIG. 7 showing the max load at suture pull-out. FIG. 8 shows the results of the stiffness test.

Using two factor ANOVA with 95% confidence intervals, statistically significant differences between suture pull-out strength of several of the samples were found for the experiments at day 0 and at day 14. The suture pull-out tests at day 0 showed that the PDS/VICRYL nonwoven with foam and the PDS 275.5 mg/cc nonwoven with foam required larger loads to pull-out the suture than the other samples. When compared to the meniscus, the other samples were statistically equivalent. The initial test also showed that the addition of foam to the nonwoven scaffolds increased the maximum load in all cases.

At day 14, the PDS/VICRYL nonwoven had a larger pull-out load than all the other samples and was followed closely by the PDS/VICRYL nonwoven with foam and the PDS 275.5 mg/cc nonwoven. The PDS 120 mg/cc nonwoven with foam and the interlock knit with foam required smaller maximum pull-out loads than the native meniscus. All other samples were statistically equivalent. The day 14 test also revealed that all the samples with foam had smaller maximum loads after two weeks.

In the day 0 stiffness tests, the PDS/VICRYL nonwoven with foam and the PDS 275.5 nonwoven with foam had statistically greater stiffness then the other samples. Again, the addition of foam provided improved results at day 0. At day 14, the stiffness results showed that the PDS/VICRYL sample had better stiffness characteristics than the other samples and that the PDS 275.5 mg/cc nonwoven with and without foam also did well. The results also shown that when compared with the day 0 results, those samples with foam components generally showed a more dramatic reduction in stiffness on day 14 than those sample without a foam component.

With the exception of the 240 mg/cc nonwoven (with and without foam), the higher density nonwovens generally performed better than the lower density nonwovens and better than the conventional implants. The test results for the 240 mg/cc nonwoven samples can be explained by the reduced thickness of the sample. The 240 mg/cc nonwoven had a thickness of only 0.5 mm compared to the 1 mm thickness of the other samples.

EXAMPLE 2

The tensile strength properties of the scaffold of the present invention were investigated and compared with conventional meniscal implant devices. Nonwoven scaffolds of various densities, with and without a foam component, were constructed from PDS and PDS/VICRYL fibers. A conventional PDS mesh reinforced with foam was used for comparison. The experiments were performed in accordance with the standards of the American Society for Testing and Materials (D638-02, *Test Method for Tensile Properties of Plastics* and D1708-02a, *Standard Test Method for Tensile Properties of Plastics By Use of Microtensile Specimens*).

The samples were prepared in the shape of a dogbone by die cutting sheets of material. The resulting samples had 5 mm widths and various thicknesses. The samples were placed in an INSTRON (Model 4210) to provide a constant rate of crosshead-movement. A video extensometer was used to measure the distance between two points on the specimen as it was stretched.

Based on the results, the following calculations were made. Ultimate tensile strength was calculated by dividing the maximum load by the original cross sectional area of the specimen. Strain at peak stress was calculated by dividing the difference between the length at the maximum load and the initial length by the initial length and multiplying by 100. Maximum strain was calculated by dividing the difference between the maximum displacement and the initial length and multiplying by 100. The modulus of elasticity was calculated by dividing the difference in stress of any segment of the initial linear portion of the stress-strain curve by the corresponding difference in the strain. Due to the composite nature of the materials, there may be more than one linear portion of interest in the modulus curve.

Figure 9:
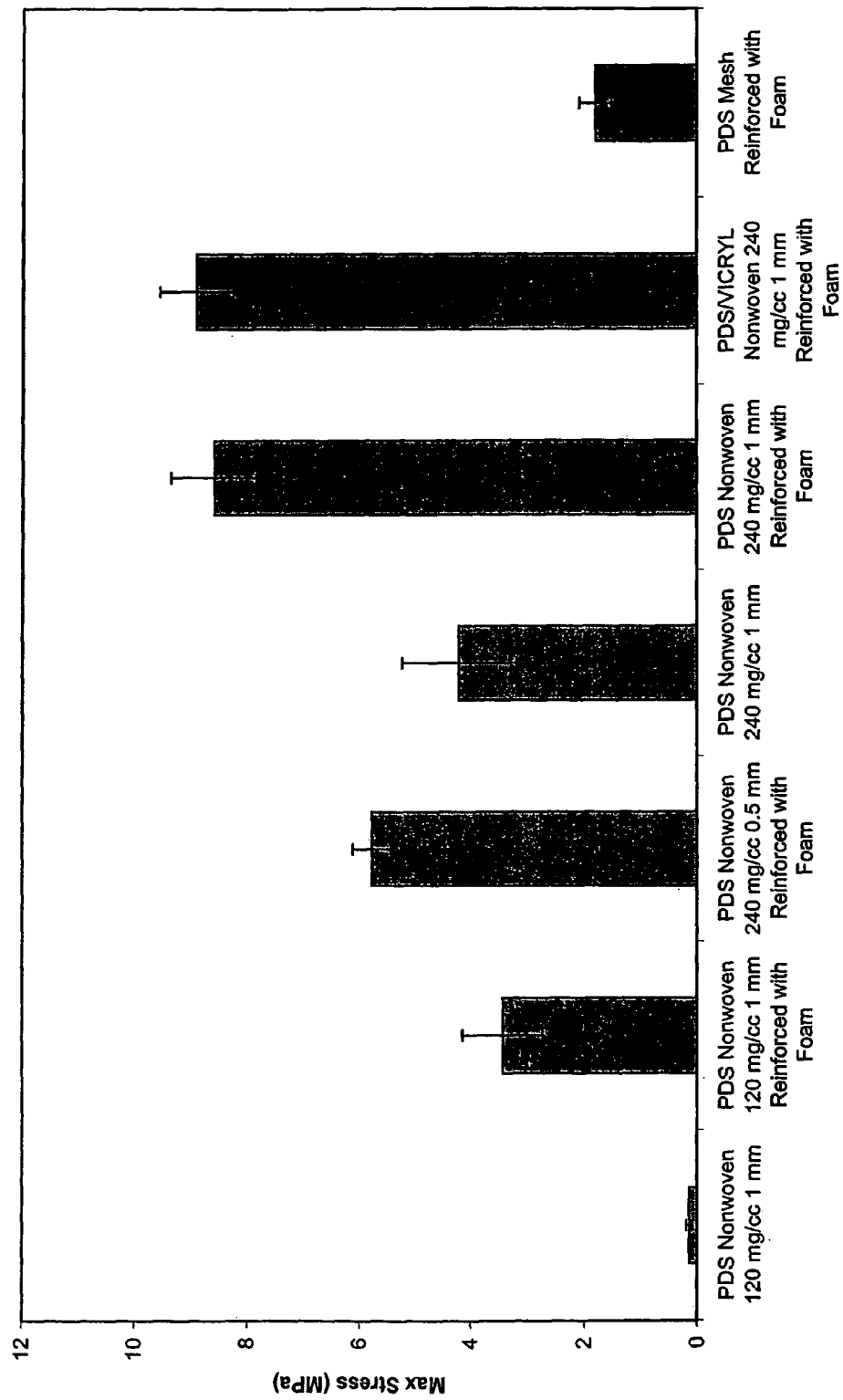
FIG. 9 is a graph illustrating the maximum stress results from Example 2.
Figure 10:
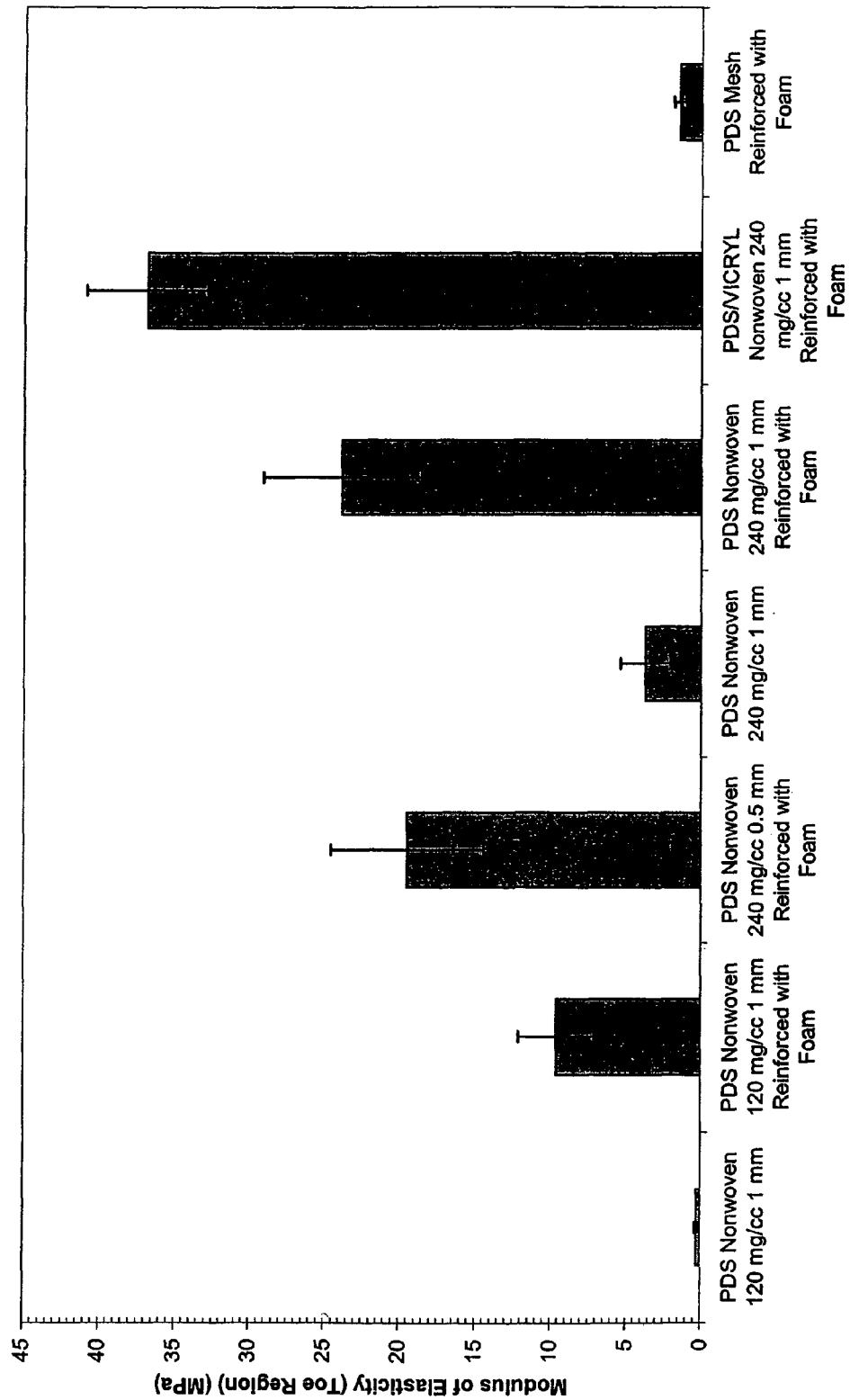
FIG. 10 is a graph illustrating the modulus of elasticity results in the toe region from Example 2.
Figure 11:
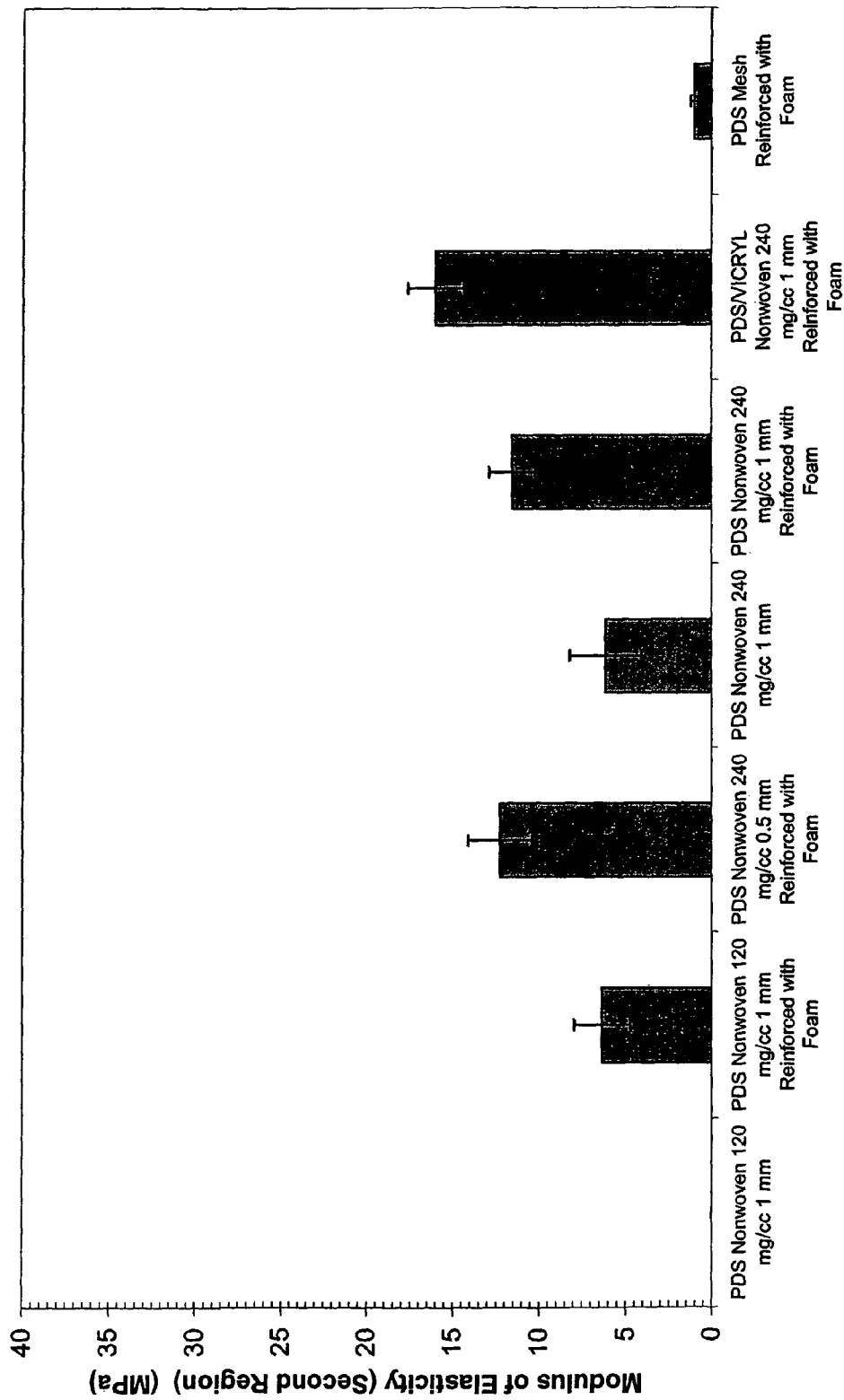
FIG. 11 is a graph illustrating the modulus of elasticity results in the second region from Example 2.

The results of the tensile tests for the various samples are illustrated in FIG. 9 (which shows a graph of maximum stress); in FIG. 10 (which shows a graph of modulus of elasticity in the toe region); and in FIG. 11 (which shows a graph of modulus of elasticity in the second region).

The results of the maximum stress test demonstrate a significantly higher load for the PDS nonwoven at a density of 240 mg/cc with foam and the PDS/VICRYL having a density of 240 mg/cc with foam, than the conventional PDS mesh reinforced with foam. The PDS nonwoven at a density of 120 mg/cc with foam also performed better then the conventional implant.

The results of the modulus of elasticity test show, that in the toe region, the nonwoven and foam scaffolds performed significantly better than the PDS mesh with foam. In addition, thicker and higher density nonwovens performed better then the other samples. In the second region, the modulus of elasticity of the nonwovens and foam scaffold also outperformed the PDS mesh and foam sample.

EXAMPLE 3

The tensile strength properties of the scaffold of the present invention were investigated for scaffolds of varying thickness and material composition. The first and second scaffold were constructed with a 50/50 mixture of PDS and VICRYL and had a thickness of 1 mm and 0.5 mm, respectively. The third scaffold was constructed from a 40/60 mixture of PDS and VICRYL and had a thickness of 0.7 mm. The nonwoven scaffolds all had a density of 240 mg/cc and did not include a foam component. The experiments were performed in accordance with the standards of the American Society for Testing and Materials (D638-02, *Test Method for Tensile Properties of Plastics* and D1708-02a, *Standard Test Method for Tensile Properties of Plastics By Use of Microtensile Specimens*).

As in Example 2, the samples were prepared in the shape of a dogbone by die cutting sheets of material. The resulting samples had 5 mm widths and various thicknesses. The samples were placed in an INSTRON (Model 4210) to provide a constant rate of crosshead-movement. A video extensometer was used to measure the distance between two points on the specimen as it was stretched.

Based on the results, the maximum load was calculated for each scaffold. In addition, ultimate tensile strength was calculated by dividing the maximum load by the original cross sectional area of the specimen. Strain at peak stress was calculated by dividing the difference between the length at the maximum load and the initial length by the initial length and multiplying by 100. Maximum strain was calculated by dividing the difference between the maximum displacement and the initial length and multiplying by 100. The modulus of elasticity was calculated by dividing the difference in stress of any segment of the initial linear portion of the stress-strain curve by the corresponding difference in the strain. In the results from Example 3, there was only one linear portion of interest in the modulus curve.

Figure 12:
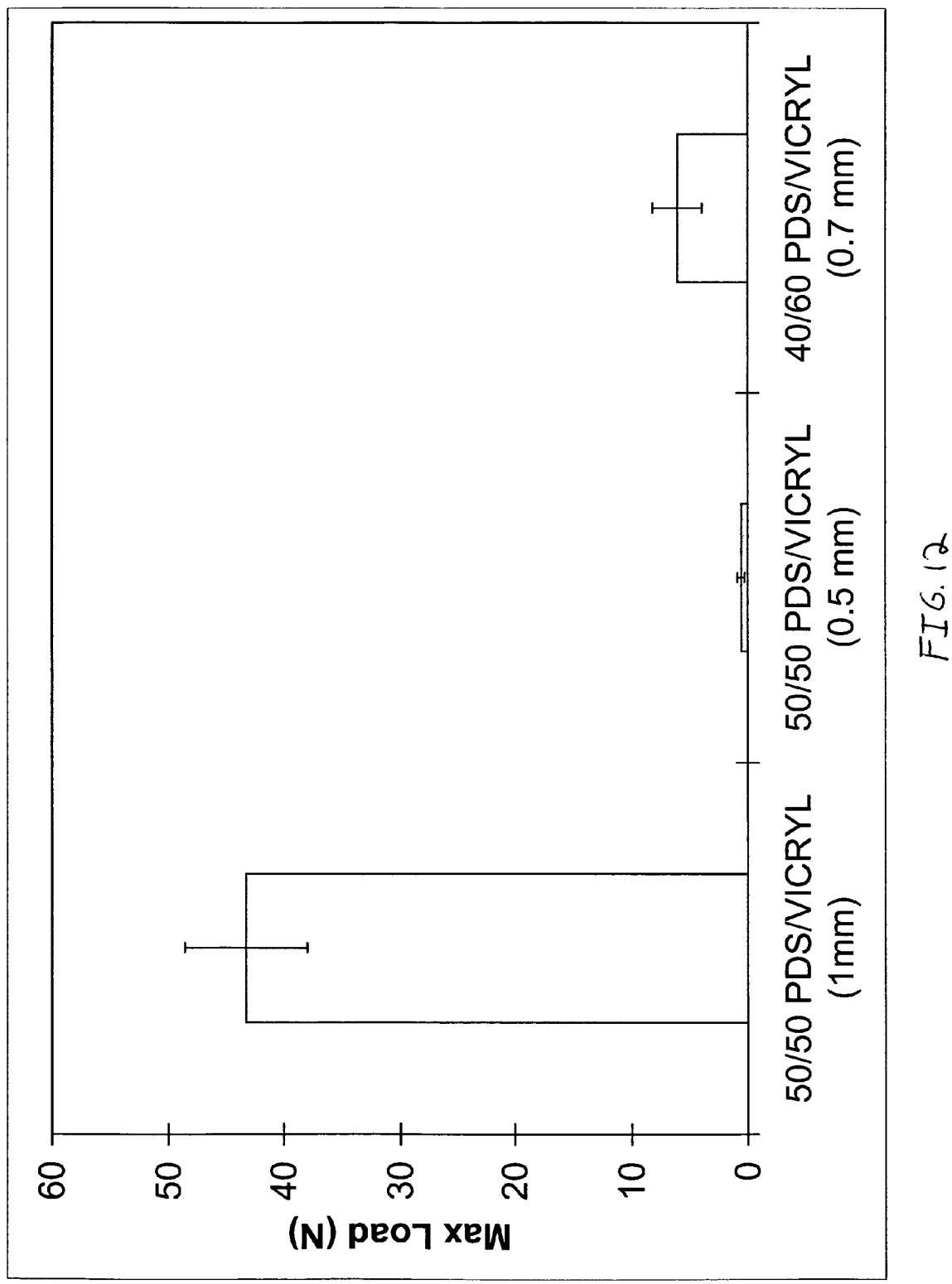
FIG. 12 is a graph illustrating the maximum load for the scaffolds in Example 3.
Figure 13:
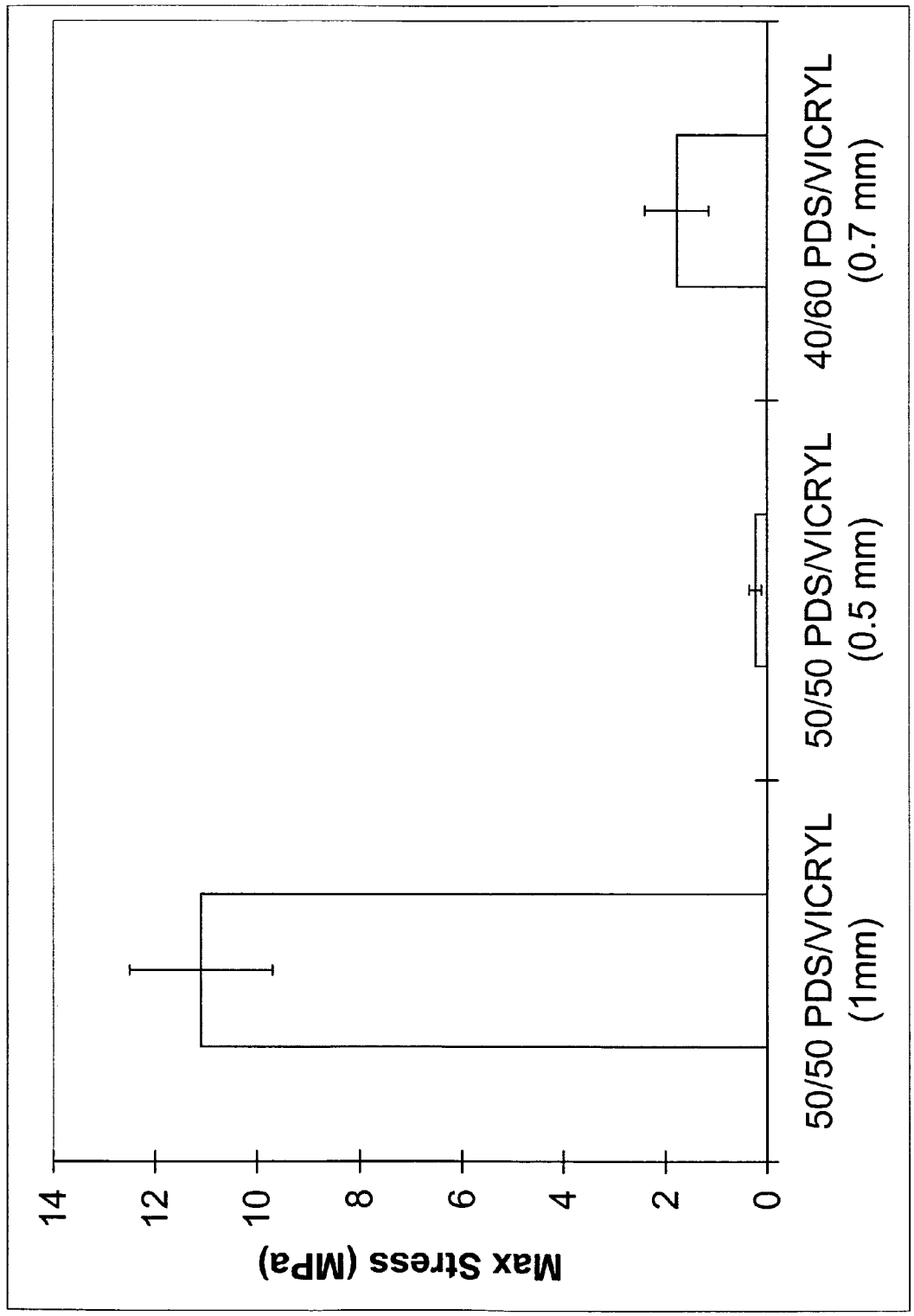
FIG. 13 is a graph illustrating the maximum stress for the scaffolds in Example 3.
Figure 14:
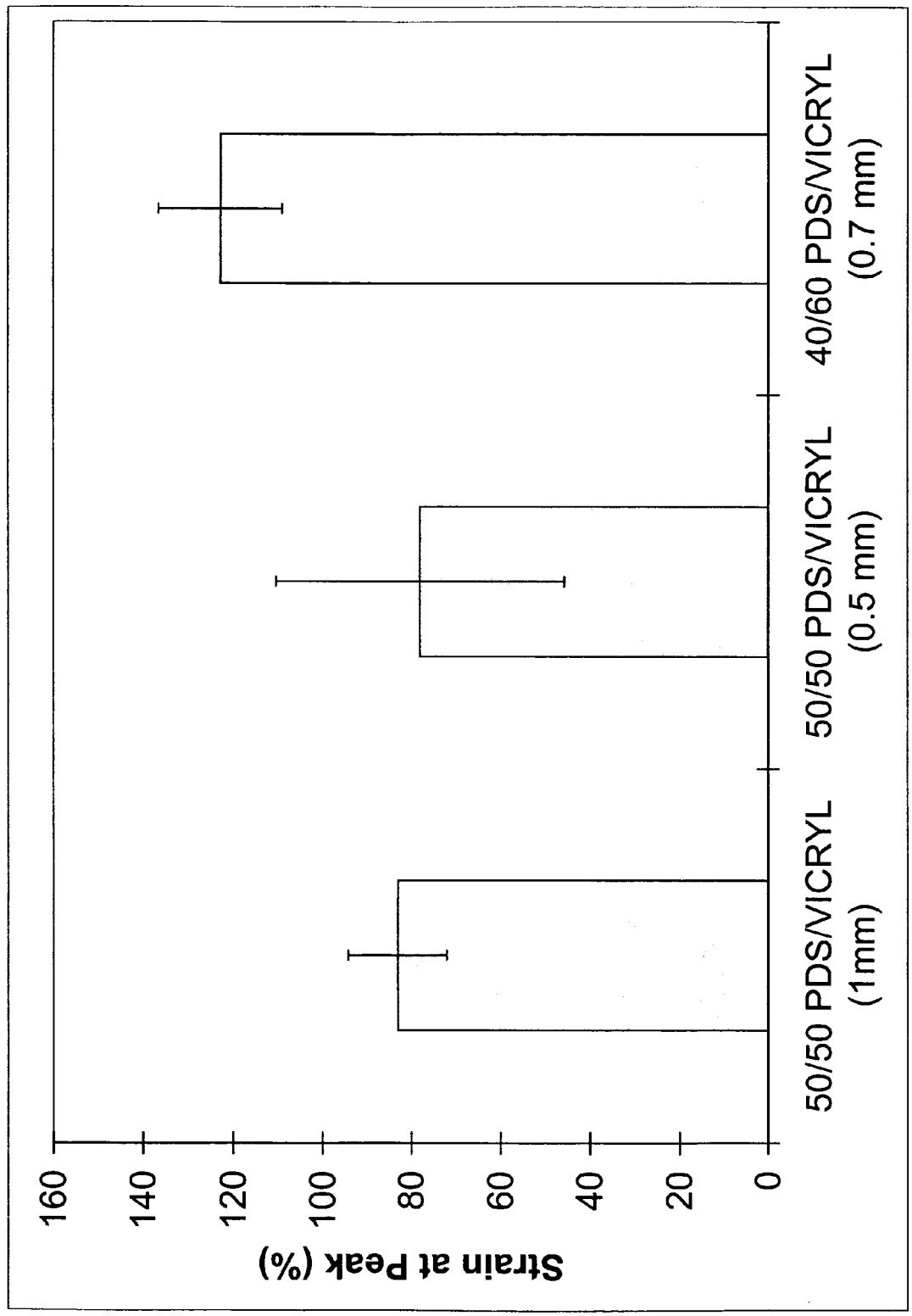
FIG. 14 is a graph illustrating the strain at peak stress for the scaffolds in Example 3.
Figure 15:
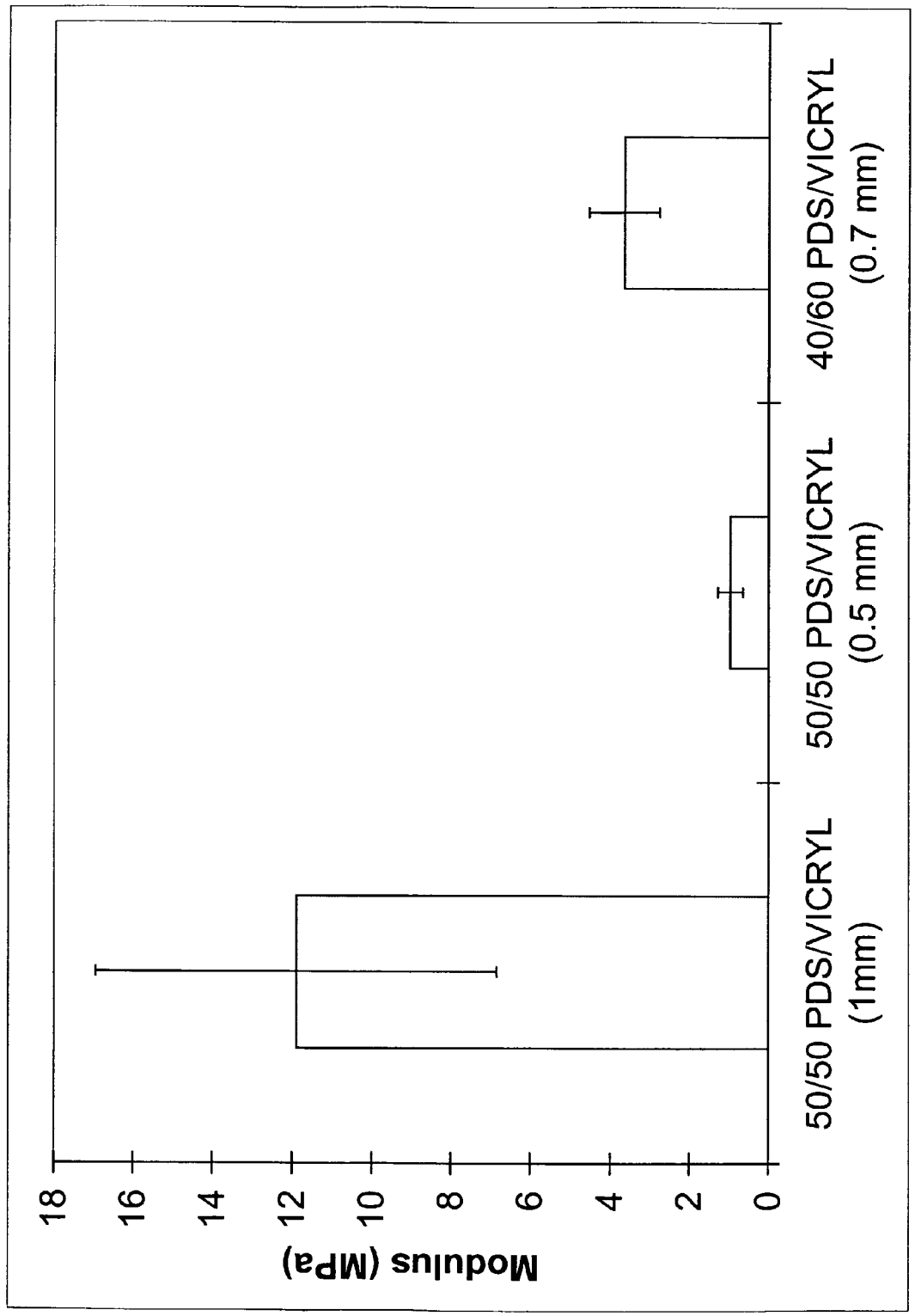
FIG. 15 is a graph illustrating the modulus of elasticity for the scaffolds in Example 3.
Figure 16:
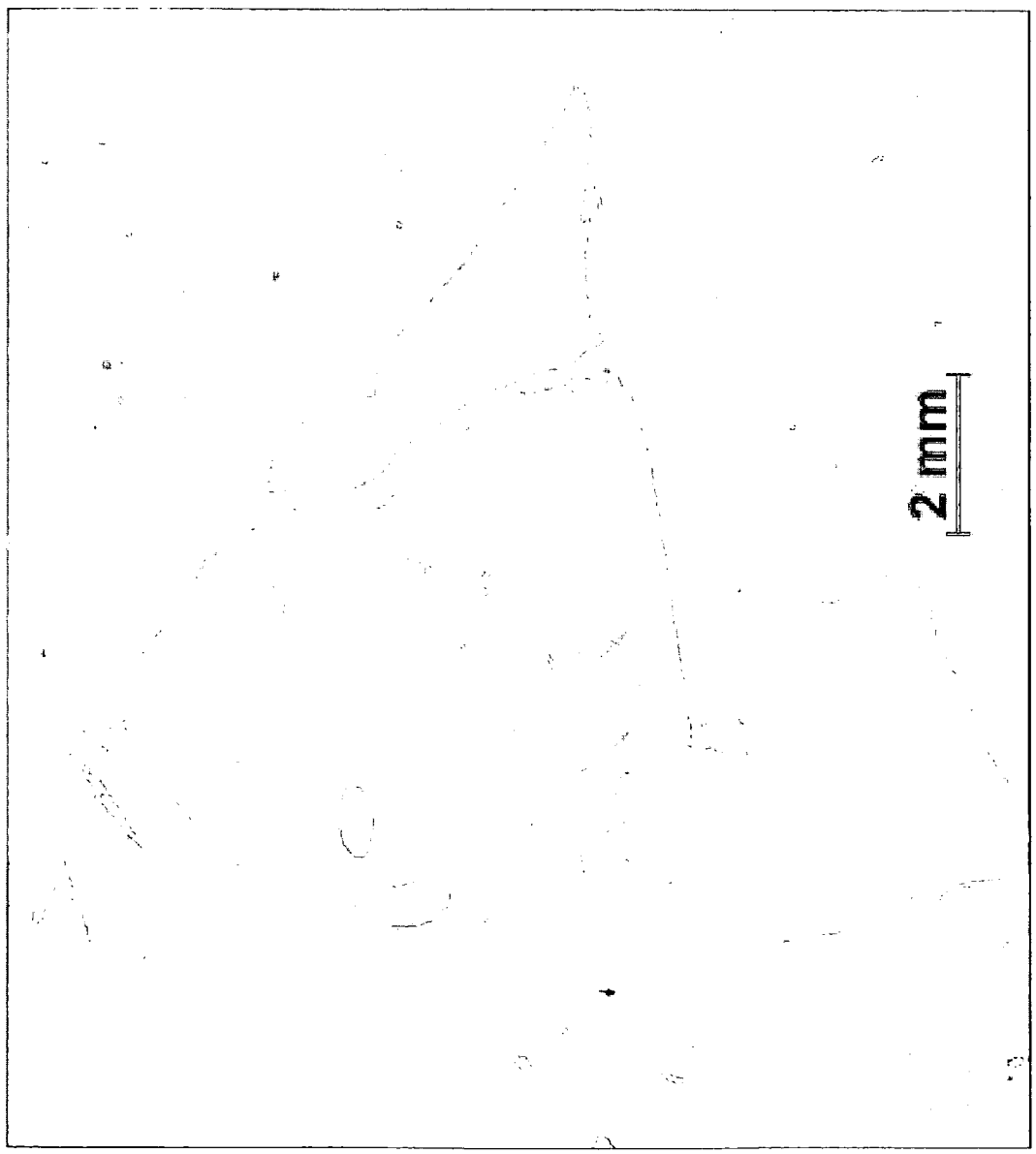
FIG. 16 is a photomicrograph of the Group 3 results from Example 4.
Figure 17:
FIG. 17 is another photomicrograph of the Group 3 results from Example 4.

The results of the tensile tests for the various samples are illustrated in FIG. 12 (which shows a graph of maximum load); in FIG. 13 (which shows a graph of maximum stress); in FIG. 14 (which shows a graph of strain at peak stress); and in FIG. 15 (which shows a graph of modulus of elasticity).

The tensile test results show desirable scaffold characteristics, especially for the thicker nonwoven scaffolds. In particular, the 50/50 PDS/VICRYL 1 mm scaffold had a max load above 40 N, a max stress above 10 MPa, and a modulus of elasticity above 11 MPa.

EXAMPLE 4

The healing potential of 50/50 PDS/VICRYL nonwovens with PRP compared to PRP alone was investigated. Twelve mature animals were divided into three groups of four animals each for repair with either a nonwoven scaffold and platelet rich plasma ("PRP") or with PRP alone. Group 1 was implanted with a 50%/50% PDS/VICRYL nonwoven scaffold (236.6 mg/cc), 1 mm thick, with 35%/65% PGA/PCL copolymer foam plus 0.5 ml PRP; Group 2 was implanted with a 50%/50% PDS/VICRYL nonwoven scaffold (236.6 mg/cc), 1 mm thick plus 0.5 ml PRP; and Group 3 was implanted with 0.5 ml PRP. The healing response was assessed grossly and histologically at 6 weeks post-implantation.

The animals used in this study were Nubian goats that weighed between 135 and 190 lbs. A medial approach to the stifle joint was made. The joint capsule on either side of the medial collateral ligament was incised. The medial collateral ligament was isolated and cut mid-substance. Using a biopsy punch, a full thickness defect (10 mm in length) was made in the avascular portion of the medial meniscus (a model for bucket handle tears). For each animal, approximately 55 ml of blood was taken prior to surgery. The platelets in the blood were concentrated to create PRP and a clot was formed from the PRP either alone or on the PDS/VICRYL nonwoven. The PRP was either placed in the defect with the PDS/VICRYL nonwoven or the PRP was placed in the defect without the nonwoven. The PRP clots, with and without the nonwovens, were stabilized with two polypropylene horizontal mattress sutures using a modified inside-out technique. The medial collateral ligament was stabilized with 2 suture anchors (Super QuickAnchor Plus with Ethibond #2, Mitek Worldwide, Norwood, Mass.) using a locking-loop suture pattern. The joint capsule was closed with a continuous suture pattern. After closing the skin, the leg was placed in a modified Schroeder-Thomas splint. The splints were removed from each animal at approximately 28 days after the surgery.

For gross analysis and histopathology study, the goats were sacrificed 6 weeks after surgery. The menisci were removed and fixed in 10% neutral buffered formalin. The samples were processed in paraffin, cut into sections and stained with Hematoxylin Eosin and Trichrome.

Results from this study showed that there was almost complete retention of the PDS/VICRYL nonwoven scaffold in the majority of animals. Vascular penetration of the scaffolds was predominantly from the abaxial surface (towards the "attached" peripheral edge of meniscus) versus the axial surface (towards the free edge). Vessels were occasionally noted along the axial border (either from vessels that had grown through the scaffold, including those that may have followed the path of a fixation suture, or from vessels associated with either femoral or tibial surface pannus that had penetrated the axial surface from the edges).

Although the "integration" of the collagen of the healing meniscal defect tissue with the native meniscal tissue was not advanced in any of these six-week sites, this feature was more advanced in Group 2 than in Group 1 overall. Integration was also advanced in the 2 of 3 Group 3 (PRP) sites that had healing tissue filling their defects. Inflammation within the repair tissue ranged from trace to slight across all sites in Groups 1 and 2, but there was slightly more tissue reaction in Group 1 sites as would be expected due to the additional presence of the foam. Birefringent fragments of foam could still be seen at all sites under polarization as would be expected for this material at 6 weeks of in vivo residence. As would also be expected at 6 weeks, the polymer scaffolds were still present. There was no evidence of infection in any of the sites.

The results of the experiment showed significant scaffold retention, versus past efforts with scaffolds in this animal model. Another promising feature especially seen in Group 2 (nonwoven scaffolds with PRP) was the amount of fibrovascular tissue ingrowth into the interstices of the scaffold.

The tissue fill characteristics for each Group was also studied by taking images of three sections of each mensical defect. The percentage tissue fill in a narrow field through the center of the defect is calculated for each region. The average of the three regions is reported as the tissue fill. FIGS. 16-23 are photomicrographs of the sampled meniscal defects for Groups 1-3.

Figure 18:
FIG. 18 is a photomicrograph of the Group 2 results from Example 4.
Figure 19:
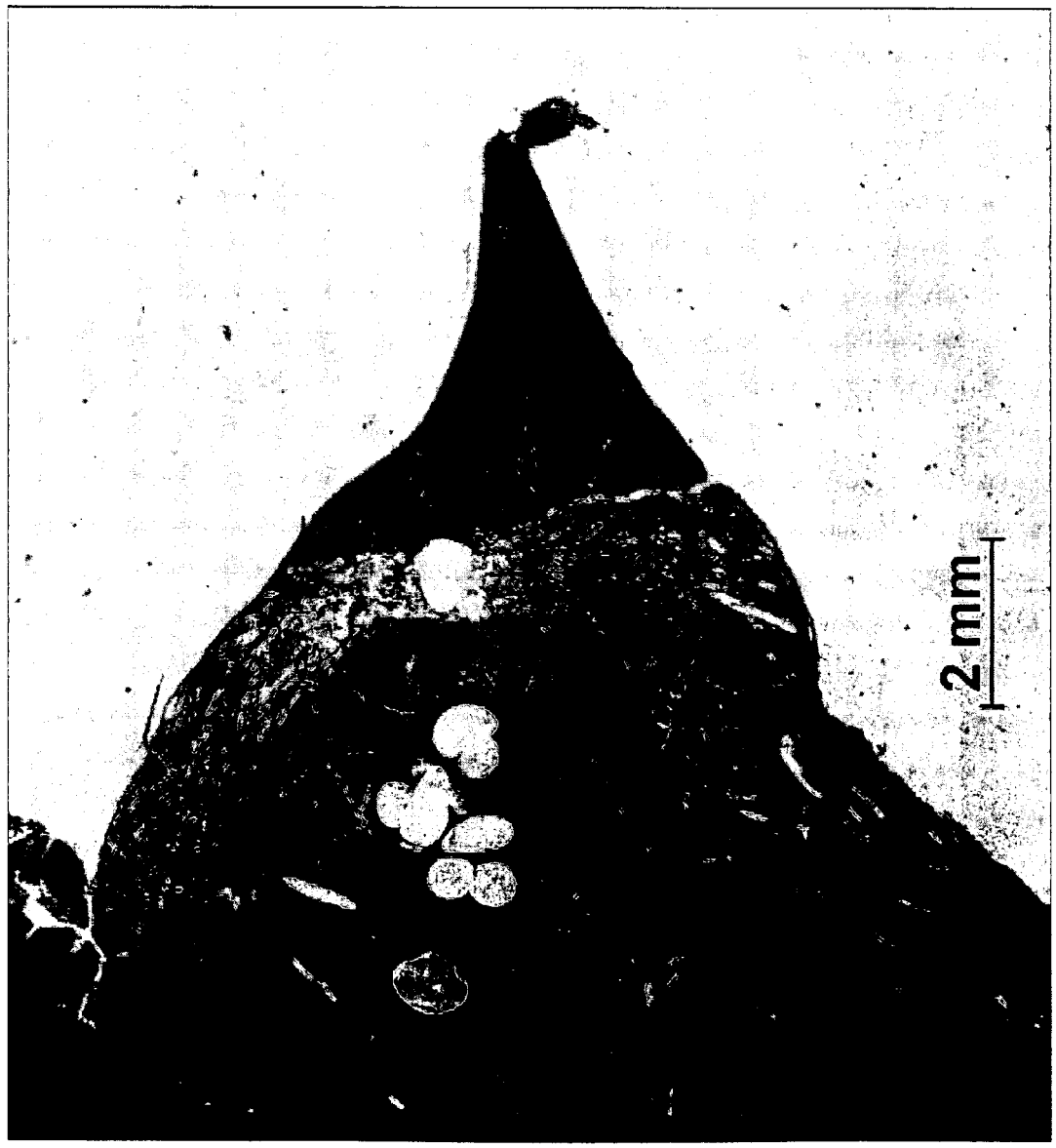
FIG. 19 is another photomicrograph of the Group 2 results from Example 4.
Figure 20:
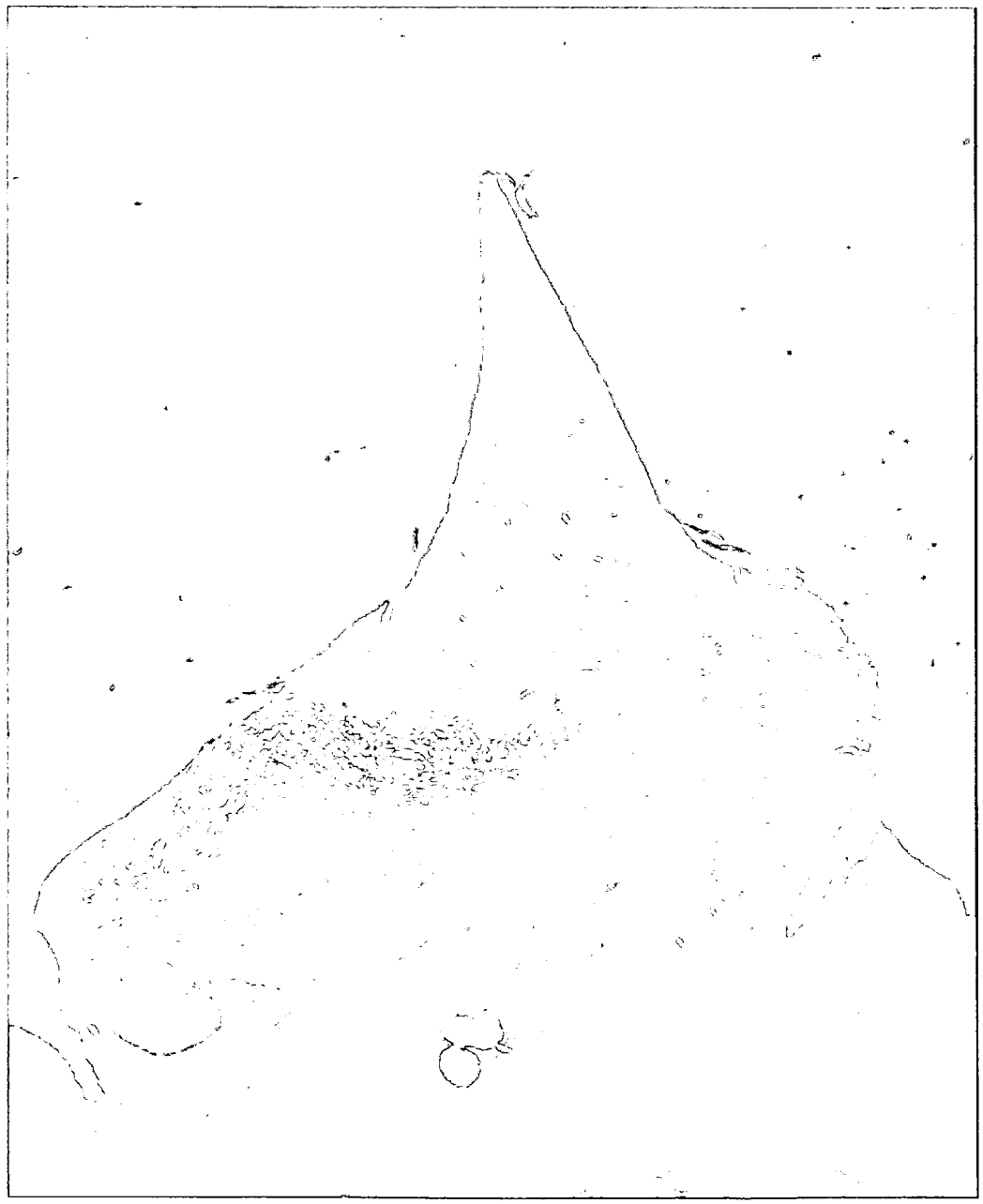
FIG. 20 is yet another photomicrograph of the Group 2 results from Example 4.
Figure 21:
FIG. 21 is a photomicrograph of the Group 1 results from Example 4.
Figure 28:
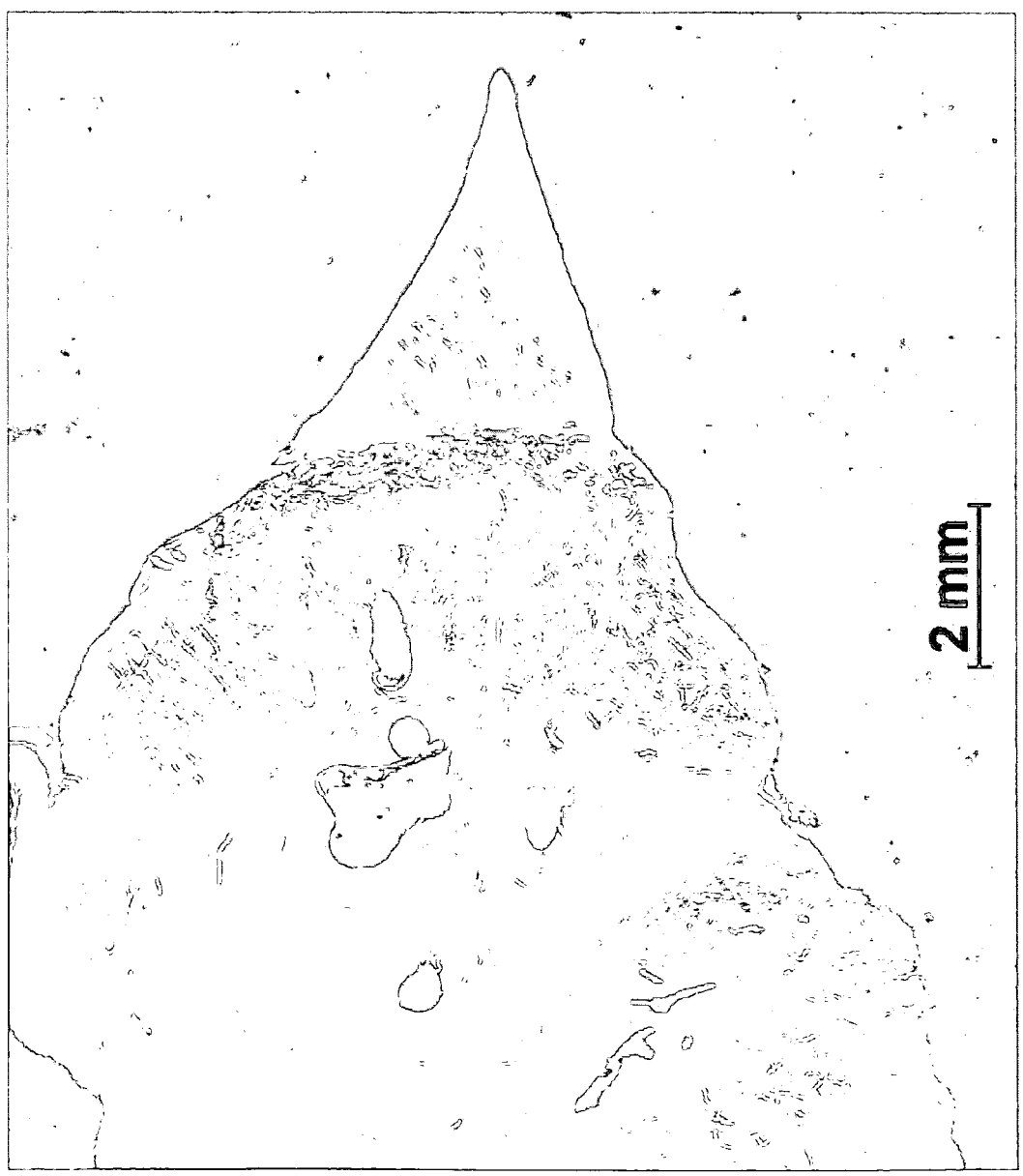
Figure 23:
FIG. 23 is yet another photomicrograph of the Group 1 results from Example 4.

The results indicate that the nonwoven scaffolds (Groups 1 and 2) help to stabilize the PRP and produce more consistent tissue fill. The tissue fill for PRP alone (Group 3) provided mixed results including 10% (poor) in FIG. 16 and 70% (good) in FIG. 17. Alternatively, the nonwoven plus PRP in Group 2 stabilized the PRP and produced consistently good or excellent results as shown in FIGS. 18-20. Finally, the Group 1 nonwoven plus foam and PRP resulted in generally good tissue fill with one outlier. The results of Group 1 are shown in FIGS. 21-23

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:
1. A biocompatible meniscal repair device, comprising;
   a biocompatible tissue repair scaffold adapted to be placed in contact with a defect in a meniscus, wherein the scaffold comprises a dry laid nonwoven polymeric material, the dry laid nonwoven polymeric material consists of a density in the range of about 120 mg/cc to 360 mg/cc, and wherein the scaffold has an initial modulus of elasticity greater than 1.5 MPa or about 1.5 MPa and an initial suture pull-out strength greater than 6 N or about 6 N, and wherein viable tissue is disposed on the tissue repair scaffold, the viable tissue having viable cells capable of integrating with native tissue adjacent to the tissue repair scaffold.

2. The repair device of claim 1, wherein the tissue repair scaffold has an initial peak stress greater than about 2 MPa.

3. The repair device of claim 1, wherein the tissue repair scaffold has an initial suture pull-out strength less than about 45 N.

4. The repair device of claim 1, wherein the tissue repair scaffold has an initial modulus of elasticity less than about 40 MPa.

5. The repair device of claim 1, wherein the tissue repair scaffold has a thickness in the range of about 0.5 mm to 1.5 mm.

6. The repair device of claim 1, wherein the tissue repair scaffold further comprises a biocompatible foam material joined to the nonwoven polymeric material.

7. The repair device of claim 1, the nonwoven polymeric material comprises a synthetic polymer.

8. The repair device of claim 1, wherein the tissue repair scaffold is bioabsorbable.

9. The repair device of claim 1, wherein the nonwoven polymeric material is formed from at least one polymer derived from monomers selected from the group consisting of glycolide, lactide, caprolactone, trimethylene carbonate, polyvinyl alcohol, and dioxanone.

10. The repair device of claim 9, wherein the nonwoven polymeric material comprises polydioxanone.

11. The repair device of claim 9, wherein the nonwoven polymeric material comprises a copolymer of polyglycolic acid and polylactic acid.

12. The repair device of claim 1, further comprising at least one bioactive substance effective to stimulate cell growth.

13. The repair device of claim 12, wherein the bioactive substance is selected from the group consisting of a platelet rich plasma, cartilage-derived morphogenic proteins, recombinant human growth factors, and combinations thereof.

14. The repair device of claim 1, wherein the nonwoven polymeric material comprises crimped, synthetic polymer fibers.

15. The repair device of claim 1, wherein the nonwoven polymeric material is heat-set.

16. The repair device of claim 1, wherein the fiber orientation of the nonwoven polymeric material is isotropic.

17. A biocompatible meniscal repair device, comprising
a biocompatible tissue repair scaffold adapted to be placed in contact with a defect in a meniscus, the scaffold including:
(a) a dry laid nonwoven polymeric material consisting of a density in the range of about 120 mg/cc to 360 mg/cc;
(b) a biocompatible foam; and
(c) viable tissue disposed on the tissue repair scaffold, the viable tissue containing viable cells capable of integrating with native tissue adjacent to the tissue repair scaffold,
wherein, the scaffold provides increased suture pull-out strength and has an initial modulus of elasticity in the range of about 1.5 MPa to 40 MPa.

18. The repair device of claim 1, wherein the viable tissue disposed on the tissue repair scaffold is selected from the group consisting of minced tissue, sliced tissue, and a tissue strip.

19. The repair device of claim 17, wherein the tissue repair scaffold has a peak stress in the range of about 2 MPa to 14 MPa.

20. The repair device of claim 17, wherein the tissue repair scaffold has a suture pull-out strength in the range of about 6 N to 45 N.

21. The repair device of claim 17, wherein the tissue repair scaffold has a thickness in the range of about 0.5 mm to 1.5 mm.

22. The repair device of claim 17, the nonwoven polymeric material comprises a synthetic polymer.

23. The repair device of claim 17, wherein the tissue repair scaffold is bioabsorbable.

24. The repair device of claim 17, further comprising at least one bioactive substance effective to stimulate cell growth.

25. The repair device of claim 24, wherein the bioactive substance is selected from the group consisting of a platelet rich plasma, cartilage-derived morphogenic proteins, recombinant human growth factors, and combinations thereof.

26. The repair device of claim 17, wherein the viable tissue disposed on the tissue repair scaffold is selected from the group consisting of minced tissue, sliced tissue, and a tissue strip.

* * * * *